(12) United States Patent
Dussi et al.

(10) Patent No.: US 9,047,545 B2
(45) Date of Patent: Jun. 2, 2015

(54) MODULAR CHEMISTRY ANALYZER

(75) Inventors: Jeannine Dussi, Arlington, MA (US); Edward Ganshirt, Lexington, MA (US); Ray Goodwin, Shrewsbury, MA (US); Stan Liffman, Newbury, MA (US); Tony Mao, Natick, MA (US); Doug Moe, Manchester, NH (US); Steve Rettew, Harvard, MA (US); Ian Smith, Nampstead, MD (US); Charlene Soley, Westford, MA (US); Le Nguyen, Dorchester, MA (US); Qian Sun, Westford, MA (US); Will Whelan, Arlington, MA (US); Diana Zipeto, Lowell, MA (US); Gregg Sweetser, Nashua, NH (US)

(73) Assignee: Medica Corporation, Bedford, MA (US)

( * ) Notice: Subject to any disclaimer, the term of this patent is extended or adjusted under 35 U.S.C. 154(b) by 566 days.

(21) Appl. No.: 11/985,077

(22) Filed: Nov. 13, 2007

(65) Prior Publication Data

US 2009/0124015 A1 May 14, 2009

(51) Int. Cl.
*G01N 35/00* (2006.01)
*G01N 35/02* (2006.01)
*G06K 19/07* (2006.01)
*G01N 35/10* (2006.01)
*G06F 3/0481* (2013.01)
*G01N 31/00* (2006.01)
*G01N 21/00* (2006.01)

(52) U.S. Cl.
CPC .......... *G06K 19/0723* (2013.01); *G01N 35/025* (2013.01); *G01N 35/10* (2013.01); *G01N 2035/00326* (2013.01); *G01N 35/00722* (2013.01); *G06F 3/04817* (2013.01)

(58) Field of Classification Search
CPC . G01N 35/00029; G01N 35/025; C40B 60/00
See application file for complete search history.

(56) References Cited

U.S. PATENT DOCUMENTS

| | | | |
|---|---|---|---|
| 5,314,825 A * | 5/1994 | Weyrauch et al. | 436/43 |
| 6,656,428 B1 * | 12/2003 | Clark et al. | 422/58 |
| 2001/0016178 A1 * | 8/2001 | Acosta et al. | 422/100 |
| 2001/0031223 A1 * | 10/2001 | Lang et al. | 422/64 |
| 2002/0137197 A1 * | 9/2002 | Ammann et al. | 435/287.2 |
| 2005/0123445 A1 * | 6/2005 | Blecka et al. | 422/64 |
| 2005/0244972 A1 * | 11/2005 | Hilson et al. | 436/47 |
| 2006/0093530 A1 * | 5/2006 | Ueda | 422/104 |
| 2007/0189925 A1 * | 8/2007 | Blecka et al. | 422/64 |
| 2007/0237675 A1 * | 10/2007 | Nichols et al. | 422/63 |

* cited by examiner

*Primary Examiner* — Jill Warden
*Assistant Examiner* — Brittany Fisher
(74) *Attorney, Agent, or Firm* — Kristofer E. Elbing

(57) ABSTRACT

A chemistry analyzer is disclosed that can include a unitary base with vertical and horizontal supports for constraining subassemblies. The subassemblies include at least a reagent/sample carousel subassembly, a transfer arm subassembly, and a reaction carousel subassembly. A centralized hydraulic system can also be provided behind a user access panel. The analyzer can use machine-readable test specifications coupled with its reagent vessels to define tests that include operations that employ the reagents. The analyzer can also display to the operator a pictorial representation that includes graphical elements that convey levels of usage for the storage vessels, and access icons that are each associated with a color and each lead to a set of screens for different types of operations for the analyzer.

18 Claims, 23 Drawing Sheets

| Name, Lot Number, and Expiration Date | Analysis Type |
|---|---|
| Reagent Volume(s) | Reagent and Sample Blanking |
| Analysis Volumes for Reagents, Samples, and Diluent | Linear Range of Assay |
| Primary and Secondary Wavelengths | Acceptable Absorbance Ranges |
| Reaction Read Times | Urine Parameters |

MODULAR CHEMISTRY ANALYZER

FIELD OF THE INVENTION

This invention pertains to chemistry analyzers for use in clinical settings.

BACKGROUND OF THE INVENTION

Chemistry analyzers are very important health care tools. They can detect imbalances in a number of chemical species in bodily fluids, such as cholesterol, glucose, enzymes, iron, magnesium, protein, uric acid, chlorine, lithium, potassium, or sodium. This information can help to diagnose a variety of conditions, such as high cholesterol, abnormal liver function, or diabetes, to name only a few. Improvements to the quality of measurements performed by chemistry analyzers could therefore have a positive effect on the care of a very large number of patients.

A chemistry analyzer is also a relatively expensive item for a health care provider, such as a hospital, and this cost is usually passed on to health care consumers. The cost that is passed on can be affected by the initial cost of the analyzer, the cost of reagents and reaction cuvettes, and the cost of maintaining and servicing the analyzer. Improvements that lead to a reduction in cost of chemistry analyzers and their maintenance could therefore have a positive effect on the overall cost of health care. And the overall health care savings resulting from even a relatively small reduction in the costs associated with an analyzer could be substantial in view of the large number of patients served by these analyzers.

The cost savings could also help make the technology available to more patients. In developing countries and remote or less affluent regions of developed countries, cost may prevent health care providers from having easy access to a chemistry analyzer. They might thus need to send samples to remote facilities, recommend that patients travel to those facilities, or even diagnose conditions without the benefits of automated chemical analysis. Improvements that lead to a reduced cost of chemistry analyzers and their maintenance could therefore have a significant effect on the availability of health care as well as the promptness and efficiency with which it can be delivered.

One common chemistry analyzer design employs two carousels and a transfer arm equipped with a probe. The first carousel carries patient samples and reagents, which can be cooled to maintain stability. The transfer arm and probe move small amounts of reagents and samples to one of a series of reaction cuvettes carried by a second, heated carousel. The reaction mixture can then be subjected to photometric tests or transferred to a module containing sensors for potentiometric analysis. A fluidic system provides fluid for sample dilution and for washing the probe and fluid lines, and an electrical system relays results and provides power and sequencing signals to the various parts of the analyzer. Other designs of chemistry analyzers utilize two or more transfer arms and probes, and two or more carousels for samples and reagents.

In existing chemistry analyzers, various parts of the analyzer are typically mounted to a metal chassis. Wires, cables, and supply and waste tubes are connected between the mounted parts, and covers surround and protect the assembled analyzer.

SUMMARY OF THE INVENTION

In one general aspect, the invention features a chemistry analyzer that includes a unitary base, for mounting a plurality of subassemblies that include at least a reagent/sample carousel subassembly, a transfer arm subassembly, and a reaction carousel subassembly. The base has vertical supports including at least one support for each subassembly, with each vertical support constraining its subassembly in the horizontal direction. It also has horizontal supports including at least three supports for each subassembly, with each horizontal support constraining its subassembly in the vertical direction.

In preferred embodiments, the horizontal supports can be each defined by a single boss. A plurality of the horizontal supports for at least one of the subassemblies can be provided by a single support surface. The vertical supports can be each defined by a single pin. The base can include two vertical supports for at least one of the subassemblies to constrain rotation of that subassembly. The base portions can include at least a paired boss and pin for each of the subassemblies, with the paired boss being positioned to protrude above the paired pin. At least two pins can define vertical supports for the reagent/sample carousel subassembly, at least two pins can define vertical supports for the reaction area subassembly, and at least one pin can define the vertical support for the transfer arm subassembly. The base can comprise a single molded base part with the horizontal supports being machined horizontal areas of the single molded base part. The analyzer can further include at least a further vertical support and a further horizontal support for a wash station subassembly. The analyzer can further include at least a further vertical support and a further horizontal support for a photometer subassembly. The horizontal and vertical supports can fully constrain each of the subassemblies independent of any fastening mechanism.

In another general aspect, the invention features a method for a chemistry analyzer that includes horizontally constraining each of a plurality of chemistry analyzer subassemblies with horizontal supports defined by an integral base, and vertically constraining each of the plurality of chemistry analyzer subassemblies with at least one vertical support defined by the integral base.

In a further general aspect, the invention features an integral base means that define a plurality of horizontal chemistry analyzer subassembly constraining means for each of a plurality of chemistry analyzer subassemblies, and at least one vertical chemistry analyzer subassembly constraining means for each of the plurality of chemistry analyzer subassemblies.

In another general aspect, the invention features a chemistry analyzer that includes a chassis for mounting a plurality of chemistry analysis sub-assemblies, a housing surrounding the chemistry analysis sub-assemblies, a user access panel on the housing, and a centralized hydraulic system area defined to house a plurality of hydraulic elements operative to handle fluid for the plurality of subassemblies in the analyzer. These hydraulic elements are located in the housing and behind the user access panel.

In preferred embodiments, the hydraulic system can include consumable hoses that are replaceable through the access panel. The system can include circuitry that permits the system to operate while the access panel is open. The chemistry analyzer can further include a drawer base that defines the centralized hydraulic system area, with the user access panel being a drawer front mounted on the drawer base.

In a further general aspect, the invention features an automated chemistry analysis method that includes receiving a modular chemistry analysis test unit that includes one or more vessels for one or more reagents, and a machine-readable test specification coupled with the vessels and defining a test that defines a test including a series of operations that employ the reagents for the vessels. The method also includes installing the chemistry analysis test unit in a first chemistry analyzer that includes one or more analysis tools and sequencing logic for sequencing instructions to be carried out by the analysis tools, and automatically retrieving the machine-readable test specification from the chemistry analysis test module and storing it for access by the sequencing logic to allow the sequencing logic to instruct the analysis tools to carry out the test defined by the test specification.

In preferred embodiments, the step of automatically retrieving can operate independent of any software upgrade for the analyzer. The machine-readable test specification can be stored in an RFID tag affixed to the vessel. The vessel is a compound multi-reagent vessel that can include subvessels for a plurality of reagents, with the machine-readable test specification including information defining operations using the plurality of reagents stored in the subvessels. The step of receiving can receive a modular chemistry analysis test unit that further includes one or more machine-readable reagent quantity values, and can further include the step of storing an updated version of the machine-readable reagent quantity values after use by the first chemistry analyzer of one or more reagents from the modular chemistry analysis test unit. The method can further include the step of installing the chemistry analysis test unit in a second chemistry analyzer that includes one or more analysis tools and sequencing logic for sequencing instructions to be carried out by the analysis tools, the step of automatically retrieving the machine-readable test specification from the chemistry analysis test module and storing it for access by the sequencing logic to allow the sequencing logic to instruct the analysis tools to carry out the test defined by the test specification, and the step of storing an updated version of the machine-readable reagent quantity values after use by the second chemistry analyzer of one or more reagents from the modular chemistry analysis test unit. The method can further include the step of installing the chemistry analysis test unit in a second chemistry analyzer that includes one or more analysis tools and sequencing logic for sequencing instructions to be carried out by the analysis tools, and the step of automatically retrieving the machine-readable test specification from the chemistry analysis test module and storing it for access by the sequencing logic of the second chemistry analyzer to allow the sequencing logic to instruct the analysis tools to carry out the test defined by the test specification.

In another general aspect, the invention features a modular chemistry analysis test unit for a chemistry analyzer that includes one or more vessels for one or more reagents, and a machine-readable test specification coupled with the vessels and identifying a series of test operations that employ the reagents for the vessels The specification includes one or more reagent quantity specifications that specify a quantity of the reagents to mix with a test sample, and one or more reaction duration specifications that specify a reaction time for the reagents and test sample.

In preferred embodiments, the machine-readable test specification can be stored in an RFID tag affixed to the vessel. The machine readable test specification can further include at least one test type specification defining a type of test to be performed. The machine readable test specification can further include at least one result value specification defining an acceptable result value for a test to be performed using one or more of the reagents. The test unit can further include a machine-readable storage area for a fill level value. The machine-readable storage area for a fill level value can be a read-write storage area. The machine-readable tag can be affixed to one or more of the vessels with an adhesive.

In a further general aspect, the invention features a machine-readable identification tag for chemistry analysis test units for use in a chemistry analyzer that includes a machine-readable test specification defining a series of test instructions for access by sequencing logic, which include one or more reagent quantity specifications that specify a quantity of reagent to mix with a test sample, and one or more reaction duration specifications that specify a reaction time for the reagent and test sample.

In preferred embodiments, the tag is can be an RFID tag. The machine readable test specification can further include at least one test type specification defining a type of test to be performed. The machine readable test specification can further include at least one result value specification defining an acceptable result value for a test to be performed according to the reagent quantity specification and the reaction duration specifications. The tag can further include a machine-readable storage area for a fill level value. The machine-readable storage area for a fill level value can be a read-write storage area. The tag can further include an adhesive area to affix the tag to a portion of the chemistry analysis test unit.

In another general aspect, the invention features a method of operating a chemistry analyzer method that includes determining usage levels associated with a plurality of storage vessels that store reagents for use by the analyzer, displaying to the operator a pictorial representation that includes a plurality of graphical elements that convey levels of usage for the storage vessels, and displaying a series of access icons that are each associated with a color and each lead to a set of screens for different types of operations for the analyzer, wherein the screens are color coded to correspond to the color associated with their respective access icons.

In preferred embodiments, the method can further include the step of identifying the contents of a plurality of storage vessels that store samples for use by the analyzer, and the step of displaying to the operator a pictorial representation that includes a plurality of elements that identify the contents of the storage vessels. The pictorial representation of the reagent vessels and the sample vessels can be part of a combined representation. The pictorial representation can be a mapped pictorial representation in which positions of the graphical elements on the display correspond to positions of the vessels in the analyzer. The pictorial representation can employ a colored bar to convey usage levels. The pictorial representation can include elements that identify the reagents in the storage vessels. The step of displaying access icons can display icons that include at least a worklist icon and a results icon. The step of displaying access icons can display icons that include at least a worklist icon and a status icon. The step of displaying access icons can display icons that include at least a results icon and a status icon. The step of displaying access icons can display icons that include a worklist icon and a diagnostics, maintenance, and/or setup icon. The step of displaying access icons can display icons that include a results icon and a diagnostics, maintenance, and/or setup icon. The step of displaying access icons can display icons that include a status icon and a diagnostics, maintenance, and/or setup icon. The step of displaying access icons can display icons that include a status icon and a diagnostics, maintenance, and/or setup icon. The step of displaying access icons can display icons that include a worklist icon, a status icon, and a diagnostics, maintenance, and/or setup icon. The step of displaying access icons can display icons that include a worklist icon, a results icon, and a diagnostics, maintenance, and/or setup icon. The step of displaying access icons can display icons that include a results icon, a status icon, and a diagnostics, maintenance, and/or setup icon. The step of displaying access icons can display icons that include a worklist icon, a results icon, and a status icon. The step of displaying access icons can display icons that include a worklist icon, a results icon, a status icon, and a diagnostics, maintenance, and/or setup icon.

DESCRIPTION OF AN ILLUSTRATIVE EMBODIMENT

Figure 1:
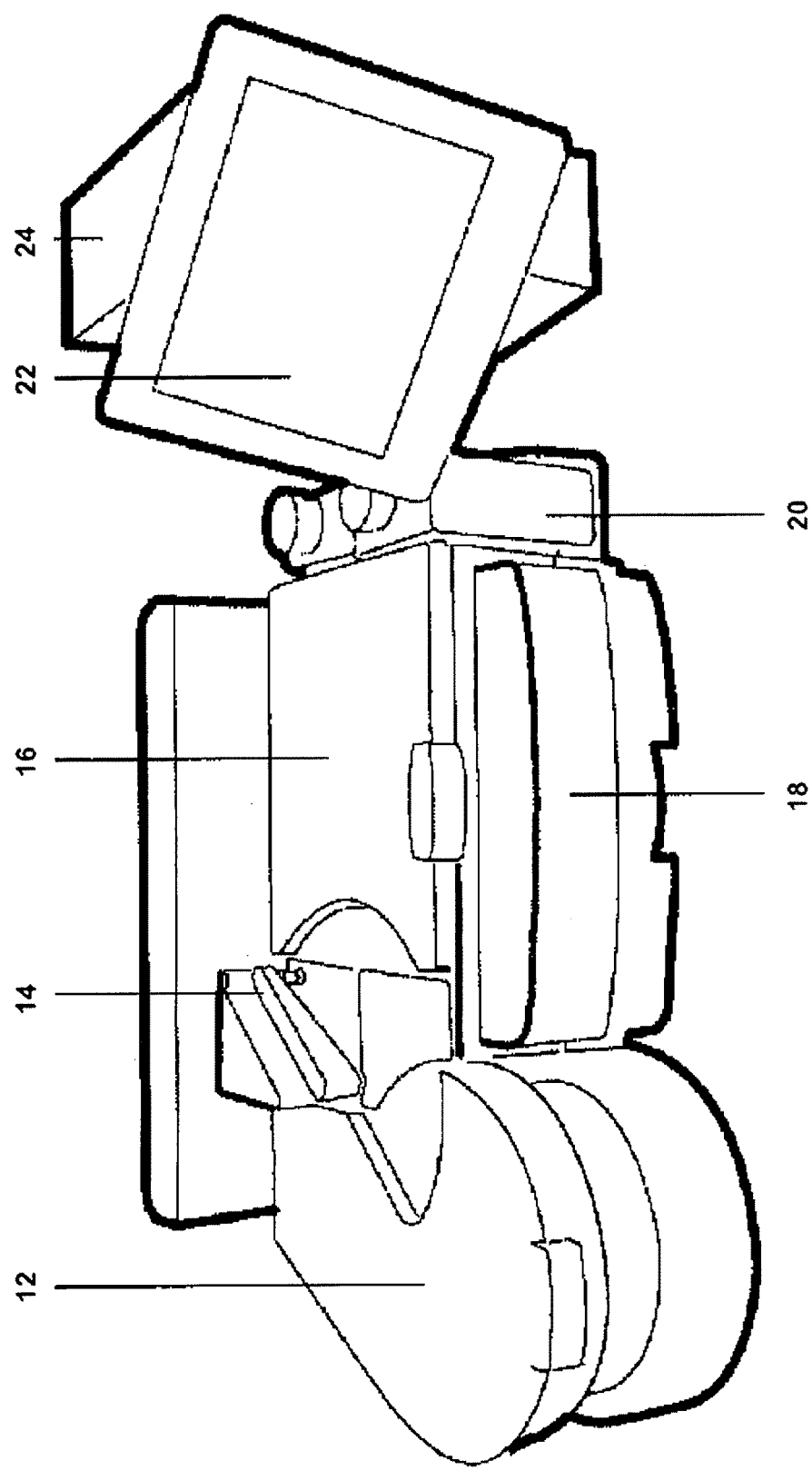
FIG. 1 is a perspective view of an illustrative modular chemistry analyzer according to the invention.
Figure 2:
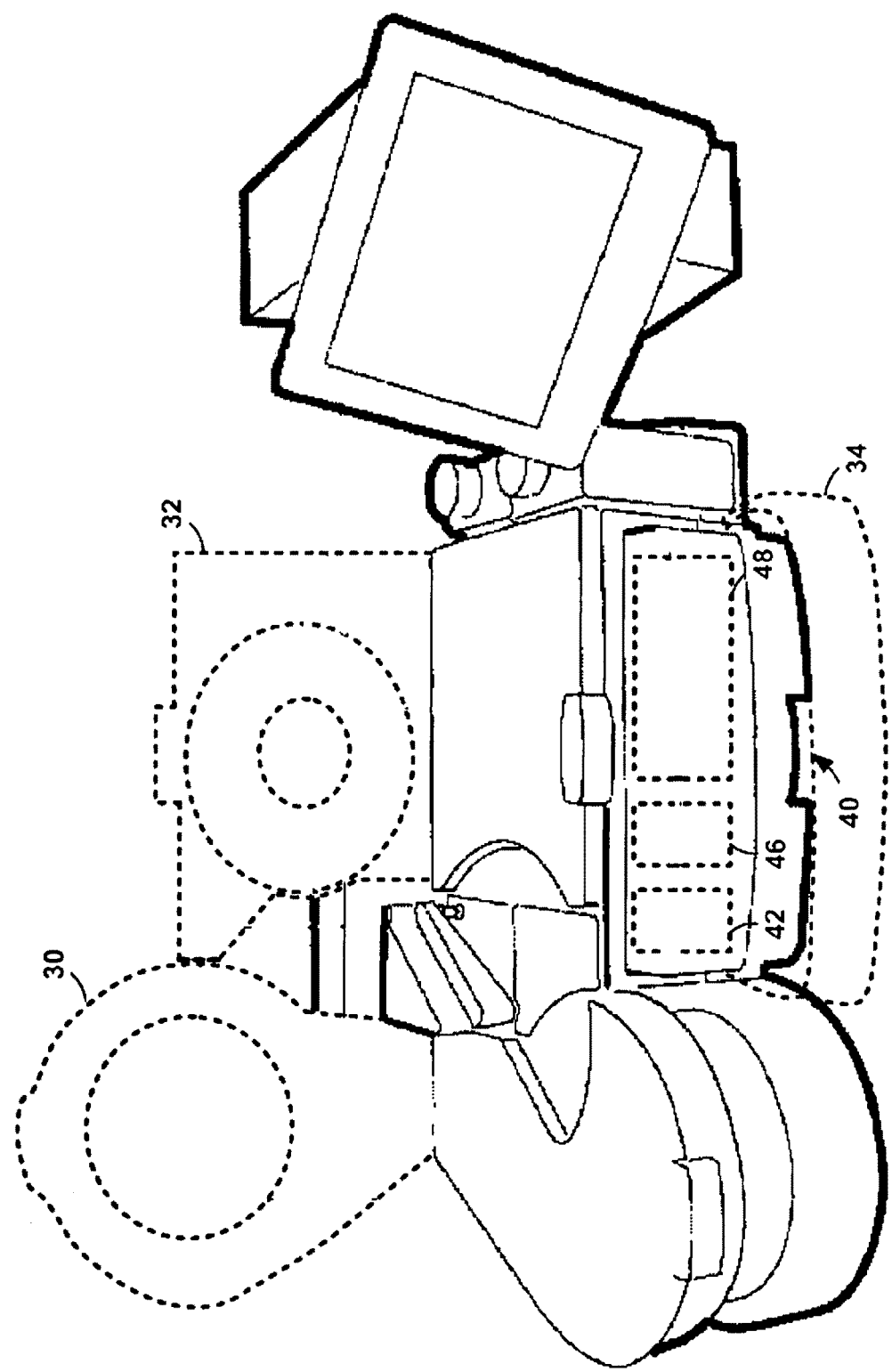
FIG. 2 is a perspective view of the chemistry analyzer of FIG. 1 showing fluidics components and covers for operator use in phantom.

Referring to FIGS. 1-2, an illustrative embodiment of a modular chemistry analyzer 10 according to the invention includes a reagent/sample area 12, a transfer arm/probe 14, a reaction area 16, a fluidics drawer 18, and a diluent/waste bottle area 20. The analyzer is also equipped with a computer 24 and a touch screen 22.

Figure 3:
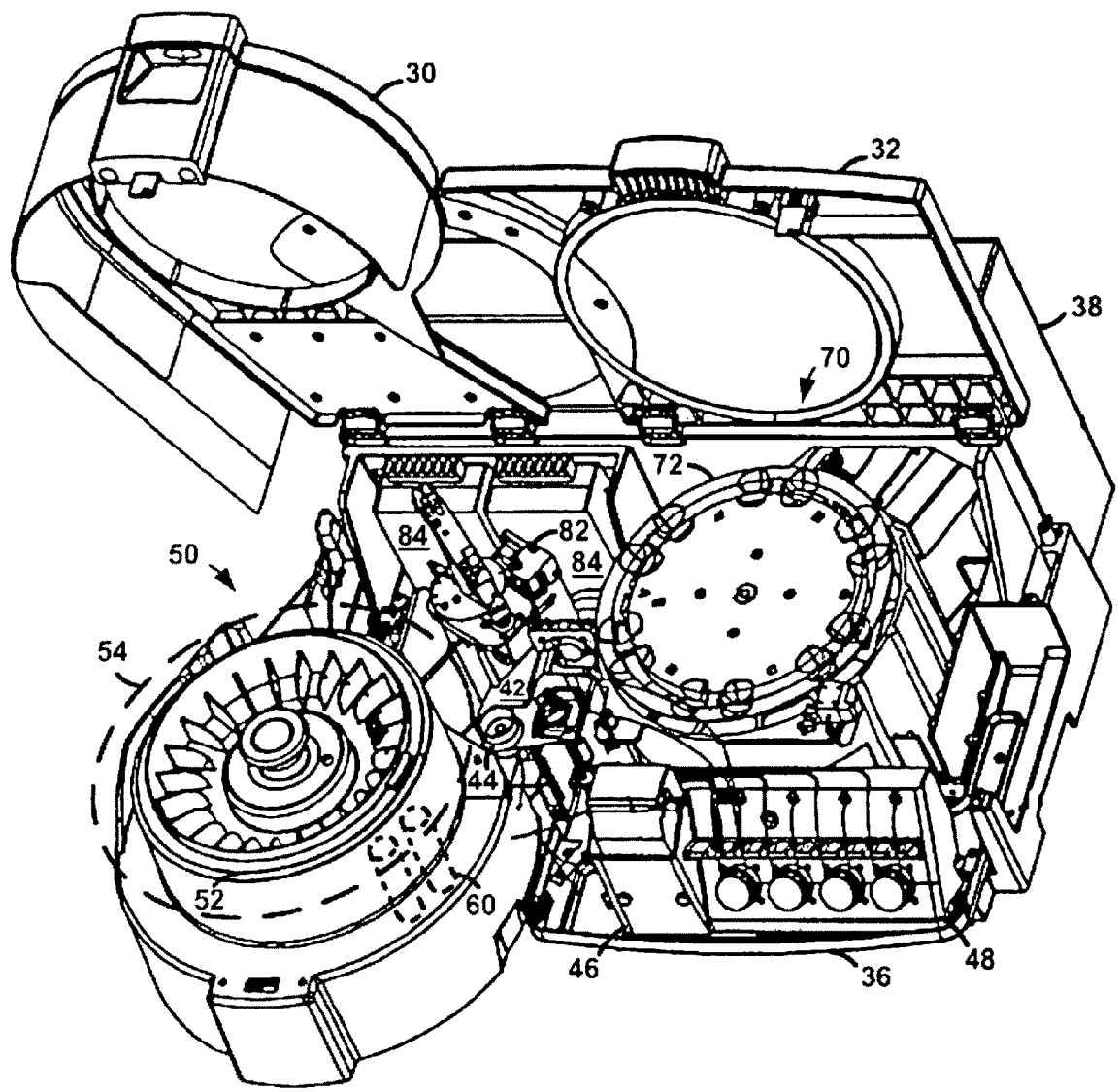
FIG. 3 is a perspective view of the chemistry analyzer of FIG. 1 with its inner cover removed to reveal functional subassemblies as accessed by service personnel.
Figure 4:
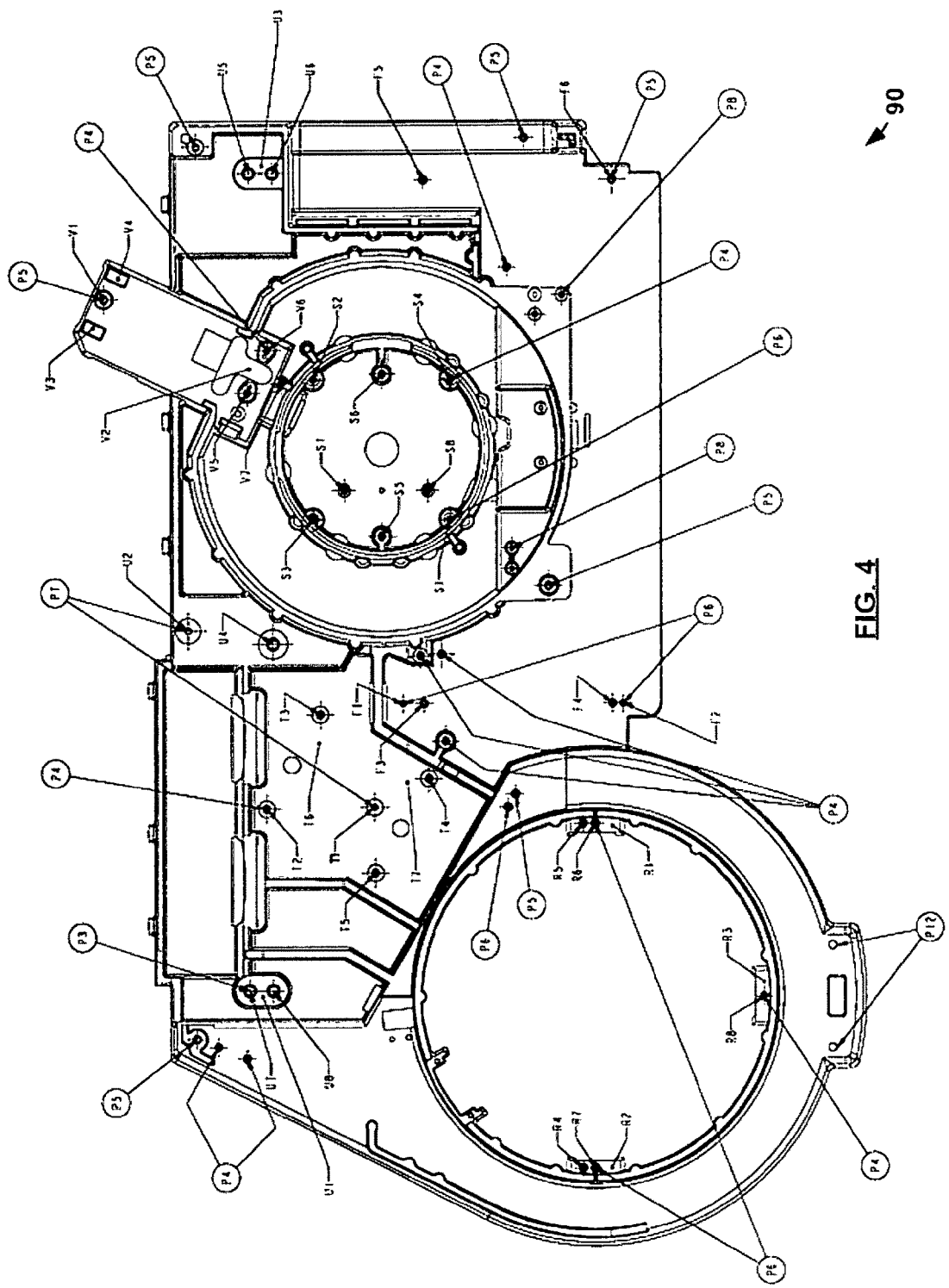
FIG. 4 is a plan view of a base for use in the chemistry analyzer of FIG. 1.

Referring to FIGS. 2-3, a first pivoting cover 30 encloses a reagent/sample carousel subassembly 50 in the reagent/sample area, and a second pivoting cover 32 encloses a reaction carousel subassembly 70 in the reaction area. A transparent pivoting fluidics drawer front 34 protects a fluidics area 40 mounted on a sliding drawer base 36. The fluidics area can include an optional module that includes a series of Ion-Selective Electrode (ISE) sensors 42 and peristaltic pumps 48. The fluidics area also includes a diluter pump 46. Mounted to the ISE sensor module is a probe wash cup 44.

Figure 10:
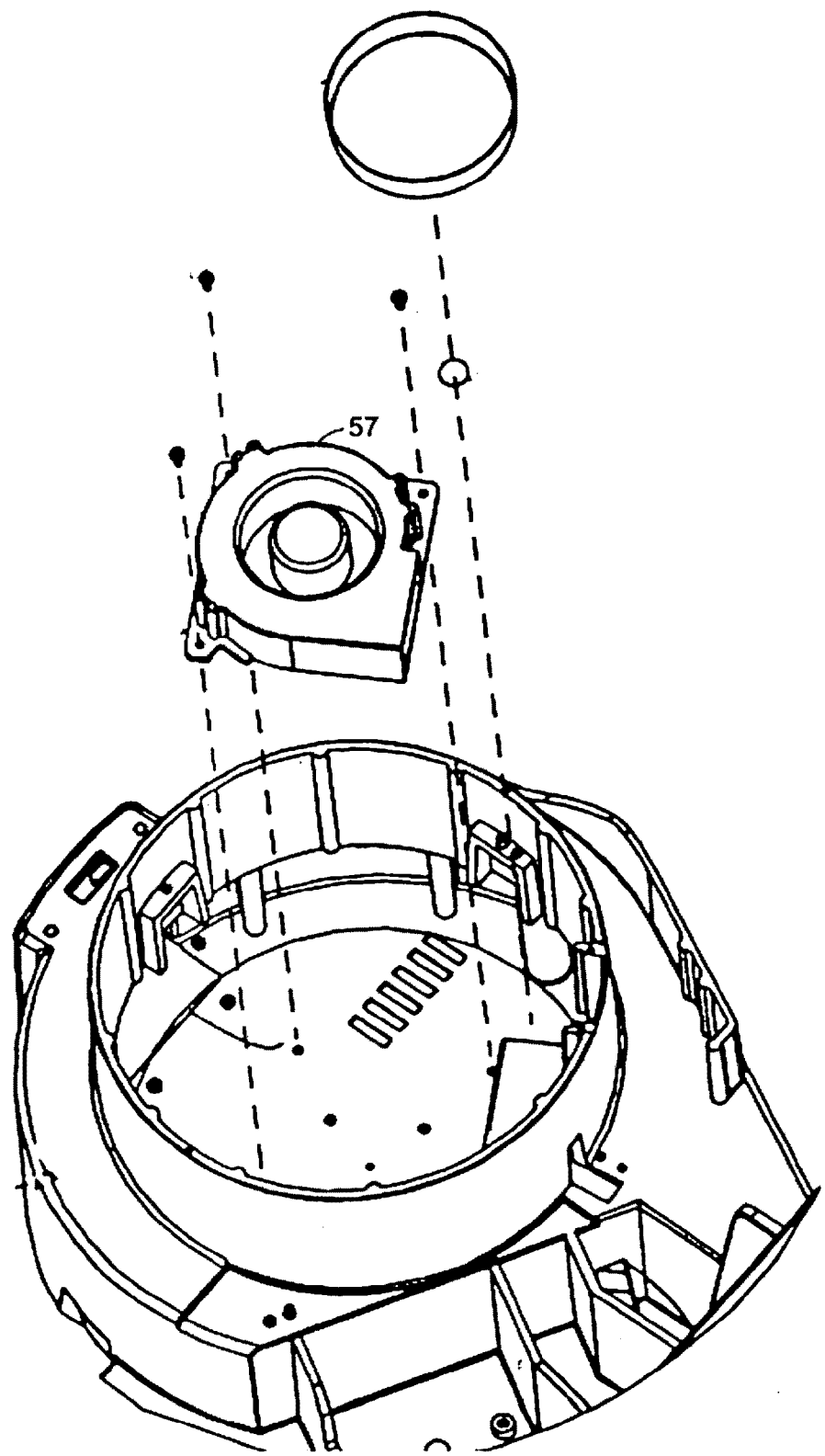
FIG. 10 is a partial perspective view of the illustrative modular chemistry analyzer of FIG. 1, showing the installation of an optional cooling unit fan in the reagent/sample area.
Figure 13:
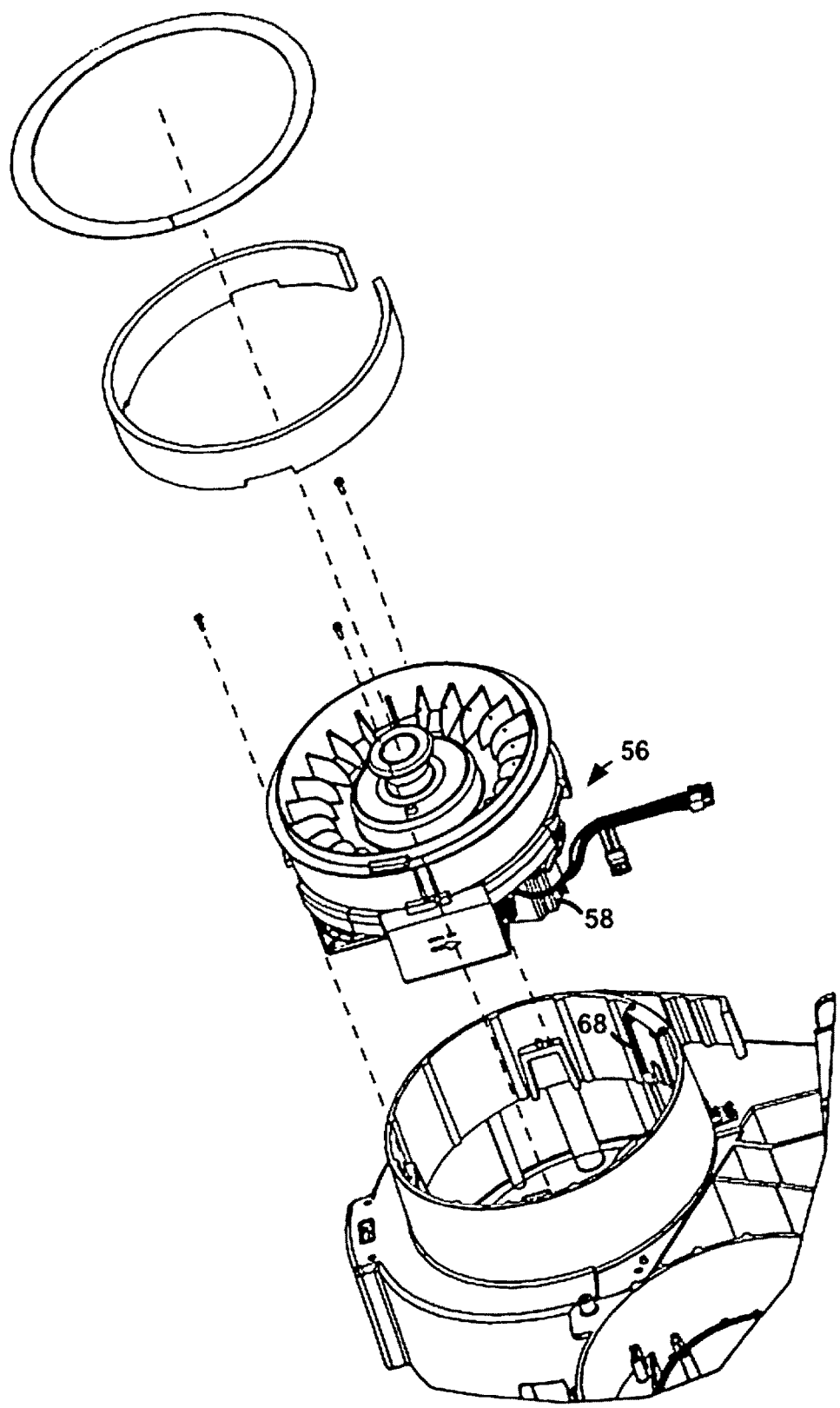
FIG. 13 is a partial perspective view of the illustrative modular chemistry analyzer of FIG. 1, showing the installation of its reagent/sample carousel subassembly.

Referring to FIG. 3, the reagent/sample carousel subassembly 50 includes a reagent tray 52 supported by a carousel drive subassembly 56 that is above an optional cooling unit 58, such as a Pelletier cooling module and its associated cooling fan 57 (see also FIGS. 10 and 13). It also includes a removable sample ring 54 that holds sample containers 60 and is loaded on top of the reagent tray, after it is loaded with reagent containers 62 during the ordinary course of operation (see also FIG. 21). A Radio Frequency Identification (RFID) reader 68 can be located in the analyzer's base adjacent the carousel drive subassembly, as well, to interact with RFID tags associated with the reagent containers. An optional bar code reader that is mounted on the base adjacent to the sample ring can read bar codes on the sample containers.

The reaction carousel subassembly 70 includes a cuvette wheel 72 mounted on a reaction carousel drive subassembly 74 adjacent a photometer 76 and above a heater 80. The transfer arm/probe 14 is part of a transfer arm/probe subassembly 82 that is positioned off-axis between the two carousels. Power supplies 84 are mounted behind the transfer arm, and an electronics subassembly 86 is mounted in a case 38 at the back of the analyzer (see also FIG. 12).

Referring to FIGS. 4-7, a unitary base 90 supports the analyzer's subassemblies in a predetermined way. The base employs supports, such as pins 94 and bosses 96 to precisely and accurately position the subassemblies (e.g., the sample/reagent subassembly). The pins are designed to interact with holes in the subassemblies to constrain them at predetermined horizontal positions (i.e., in the x- and y-directions). The bosses are designed to position the subassemblies at predetermined heights (i.e., in the z direction). The unitary molded base and pins and bosses minimize stack-up between the elements and greatly reduce the manufacturing and assembly costs of this embodiment.

Figure 5A:
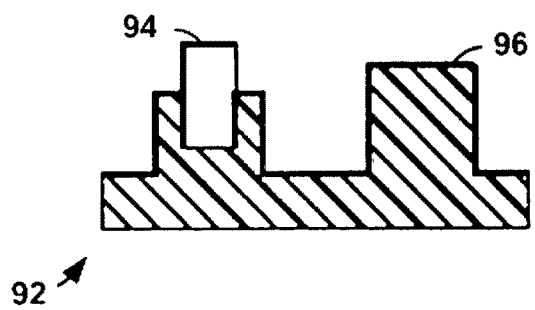
FIG. 5A is a cross-sectional view of a boss-pin pair for the base of FIG. 4.
Figure 5B:
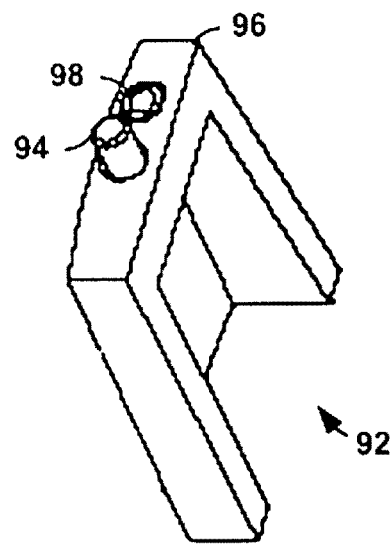
FIG. 5B is a cross-sectional view of a another type of boss-pin pair for the base of FIG. 4.
Figure 5C:
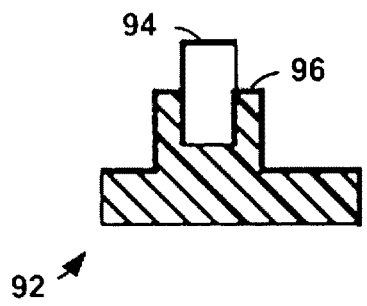
FIG. 5C is a cross-sectional view of a further type of boss-pin pair for the base of FIG. 4.
Figure 6:
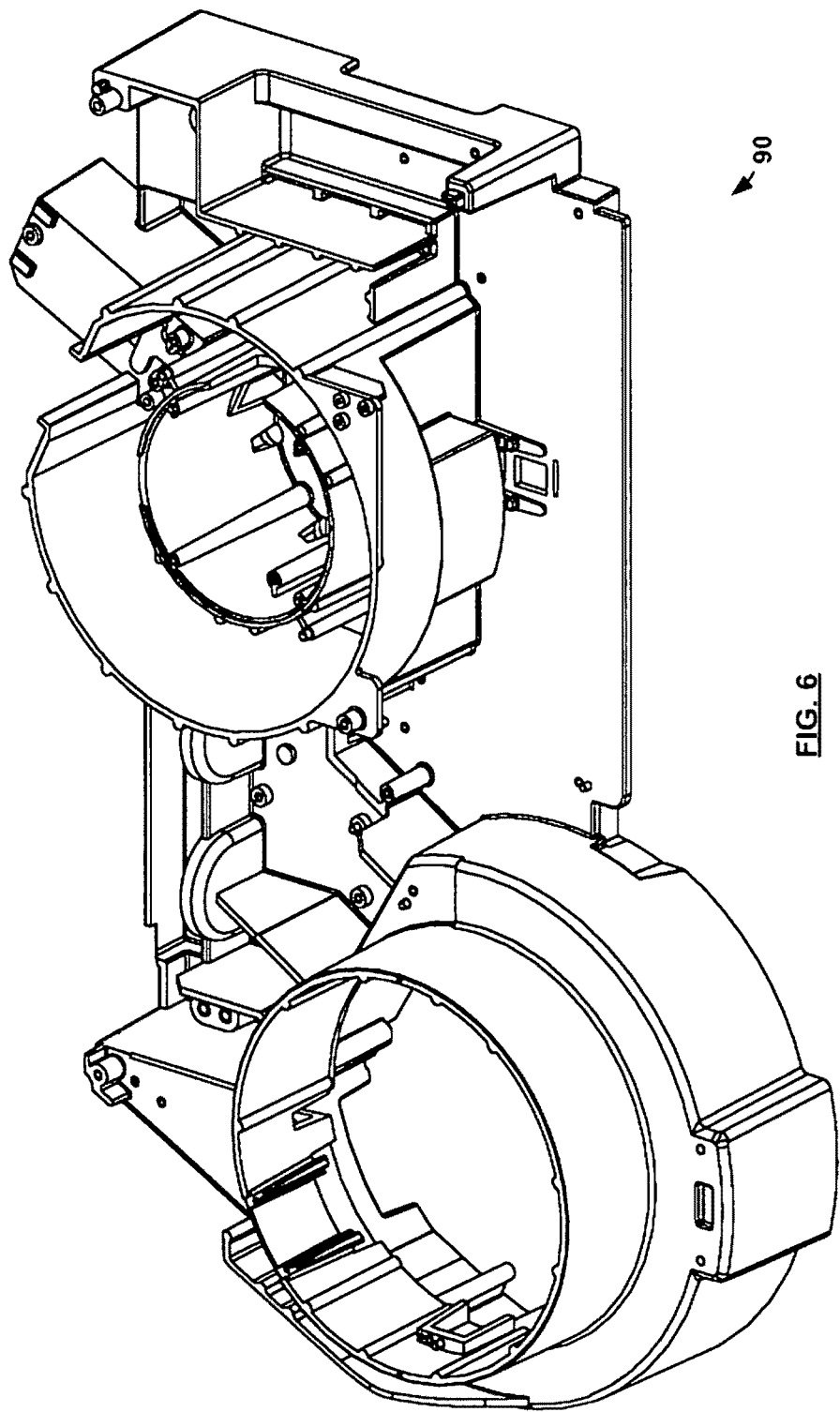
FIG. 6 is a front isometric view of the base of FIG. 4.
Figure 7:
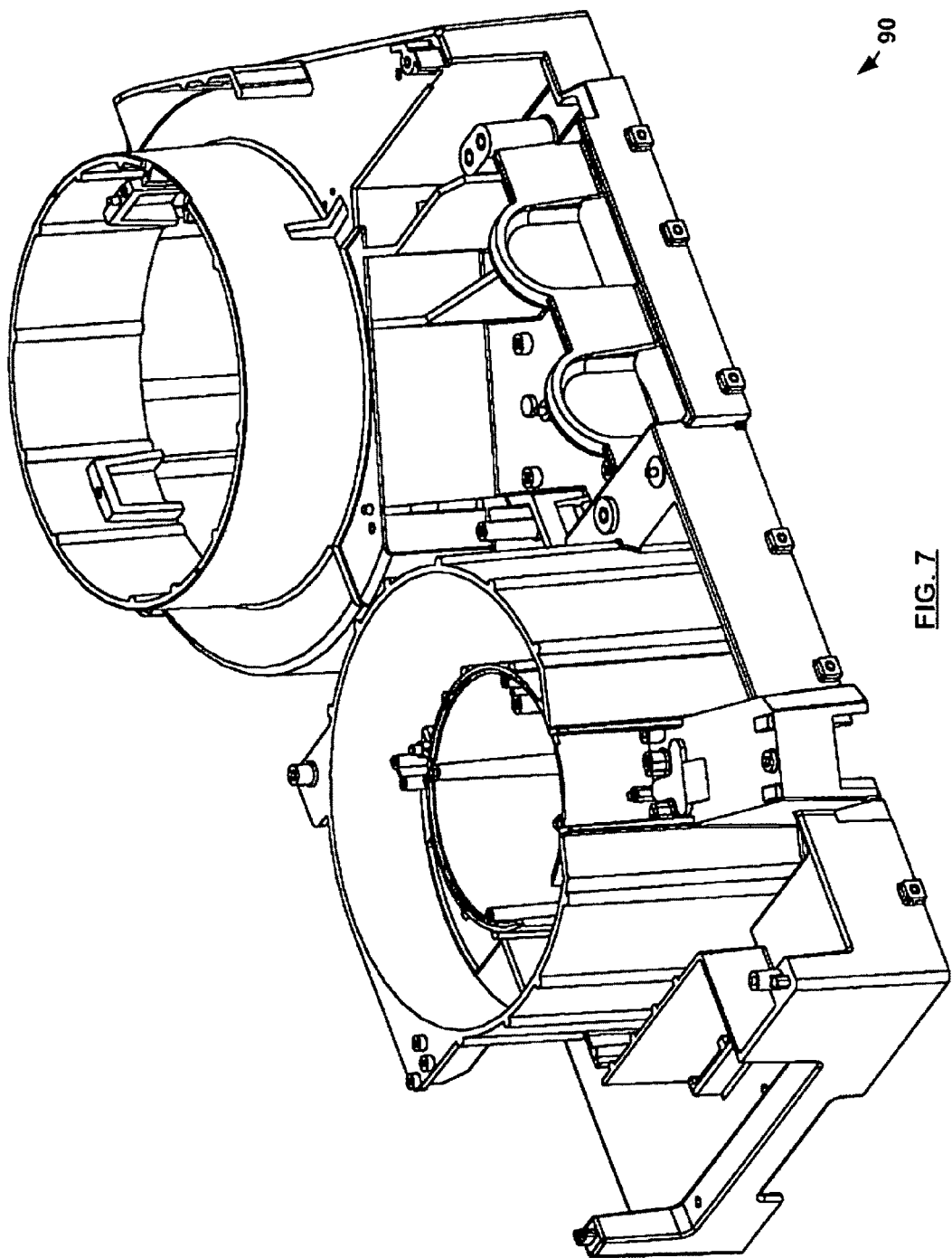
FIG. 7 is a rear isometric view of the base of FIG. 4.

The pins 94 and bosses 96 can be provided in different types of pairs 92 as shown in FIGS. 5A-5C, but they can also be placed at separate locations. A pin and boss may be paired to provide horizontal constraint as well as vertical constraint, as illustrated in FIG. 5C.

A support is a part or portion of a part, such as the base, that provides an opposing force to a point on a subassembly. The minimum number of supports required is defined by the number of degrees of freedom that need to be constrained. An object that is otherwise unconstrained, for example, would require at least two vertical supports, such as two pins, and three horizontal supports, such as three bosses. One pin would prevent horizontal translations, but not rotation, and a second pin would fully constrain a subassembly in the x-y plane. And, like a stool generally requires at least three legs, three point bosses are used to support an otherwise unconstrained subassembly in the z-direction.

Some subassemblies may only need to be partially constrained, or may not need to be constrained at all. The analyzer's power supplies, for example do not need to be constrained precisely, so there is no need to provide pins and bosses for them. Other subassemblies could be constrained precisely in one or more directions, but not in one or more others. And while cost dictates that it is generally preferable to use a minimum number of pins and bosses to achieve a set of target constraints, additional pins and bosses could also be used in some circumstances, such as to support a large or flexible subassembly. In some situations it may even be possible to provide one precisely shaped larger surface to define two or more supports at different positions. Other types of precisely dimensioned vertical constraints could also be provided, such as irregularly shaped pins or precisely dimensioned blades, teeth, or walls.

Screws can secure the constrained subassemblies in place but are not appropriate for aligning the subassemblies. This is because screws need room to move within their holes, they are typically not manufactured with a high degree of precision, and they may be replaced in the field with similar-looking but differently dimensioned screws. The act of installing screws can sometimes also damage their through holes, especially if the subassembly is not precisely positioned before installation begins. The screws therefore only serve to secure the subassemblies and can cooperate with tapped inserts 98, which can be located in the bosses. Other types of fastening arrangements could also be employed, such as cams, clamps, or barbs. The pins and horizontal supports used for the base in one embodiment are listed in table 1.

| Subassembly | Description |
|---|---|
| Transfer arm | Single pin lines up with axis of rotation of transfer arm, and minimum of three horizontal supports. |
| Reaction carousel | Minimum of two pins and three horizontal supports |
| Reagent/sample carousel | Minimum of two pins and three horizontal supports |

The use of pins, bosses, and other ways of providing supports can allow for easy assembly and very high precision positioning of subassemblies, at a relatively low cost. In one embodiment suitable for prototyping or small runs, for example, the base is first molded in a conventional manner, such as using a conventional cast urethane process. Holes for the pins and the upper boss surfaces are then precisely machined using a numerical milling machine. While the precision machining can add some cost to the base, this cost amounts to a relatively small portion of the overall cost of the analyzer, and it is offset by several benefits. In another embodiment suitable for larger runs, adequate tolerances have been achieved, without machining, using Noryl, a Polyphenylene Oxide (PPO) engineering thermoplastic available from General Electric.

A first benefit of the base construction is that it makes the analyzer easy to assemble and service. Assembly technicians and field service technicians can quickly position a subassembly by first aligning holes in the assembly with the pins that constrain it and then dropping the subassembly into place. Getting the pins and holes to line up is an operation that has is very definite feel to it, so the technician immediately knows the part is properly engaged. And once engaged, the subassembly is perfectly positioned, so there is no need to adjust its position during assembly. The analyzer can also be built to be assembled and disassembled with a single tool, such a number two Phillips screwdriver.

Simplifying assembly can also reduce the length and complexity of service and subassembly replacement tasks, and thereby allow them to be performed by less skilled personnel, such as sales representatives or even hospital staff. This can significantly reduce the cost of these tasks, particularly in remote areas. And simplifying service tasks can reduce the complexity of service manuals, which can then be more easily translated.

Another benefit of the unitary base construction is that it can reduce or eliminate the need for calibration of the transfer arm. With the subassemblies positioned precisely relative to each other, the transfer arm may be able to employ a preset travel range. It therefore need not go through an initial calibration routine or be "taught" by a technician where its different landing points are. If a calibration step is still needed, this step may be designed to take less time than might otherwise be required.

The molded base 90 is designed to eliminate tolerance stack-up in this embodiment. This can be achieved by carefully designing the order and reference points for distance measurements used in cutting the base mold. Basing measurements from the transfer arm axis pin T1 to pins that constrain the probe's service points, for example, will avoid the accumulation of tolerances that could result if the position of all of these pins were to be based on an arbitrary reference. This contrasts with the difficulties and expense that appears to have been required in prior art designs to control tolerance stack-up between probe, reagent containers, sample containers, reaction cuvettes, probe wash station, and other elements. The use of plastic in the base also reduces thermal expansion errors in this embodiment.

Figure 8:
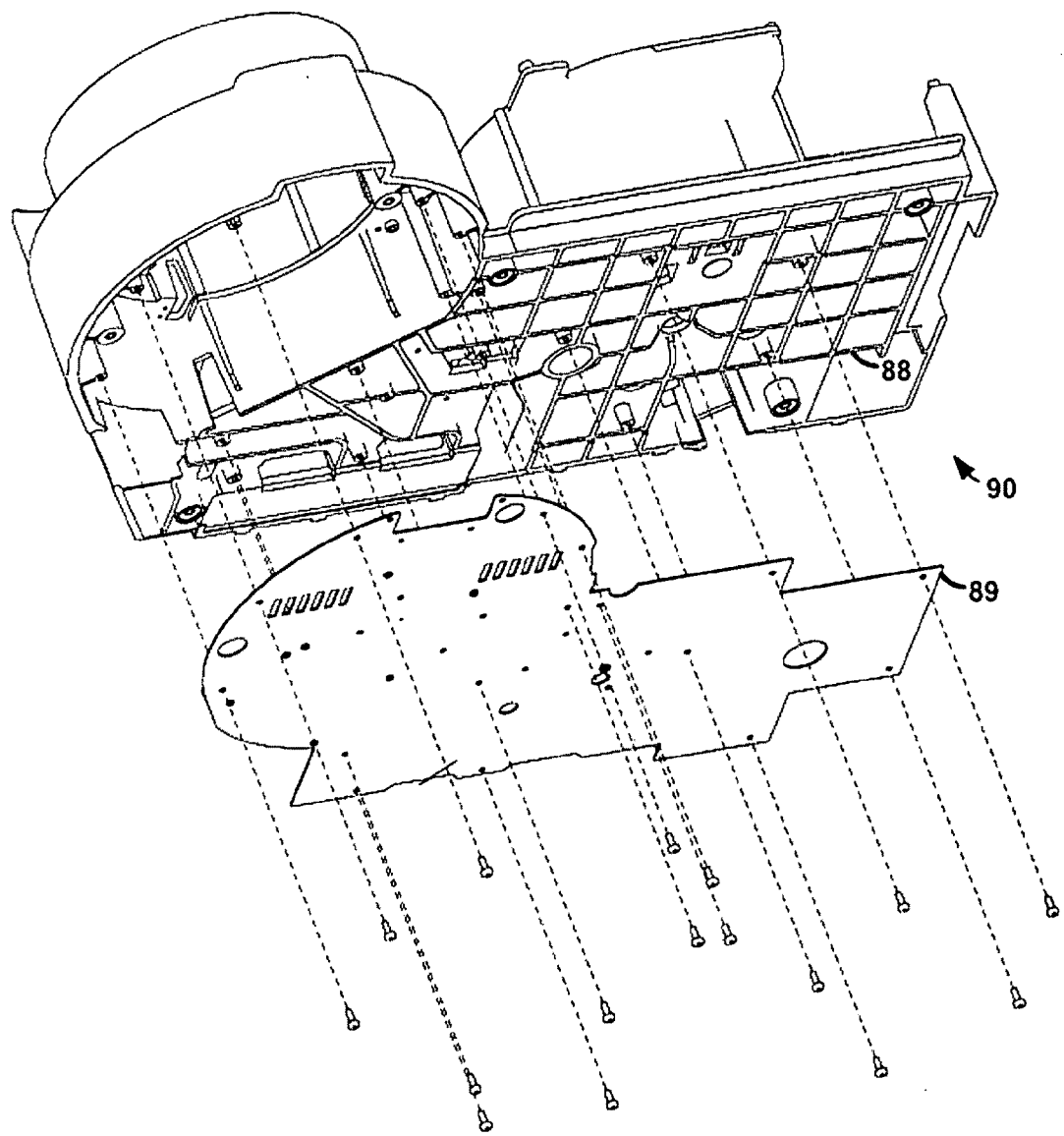
FIG. 8 is an exploded assembly drawing showing the bottom of the base of FIG. 4 and its stiffening plate.
Figure 9:
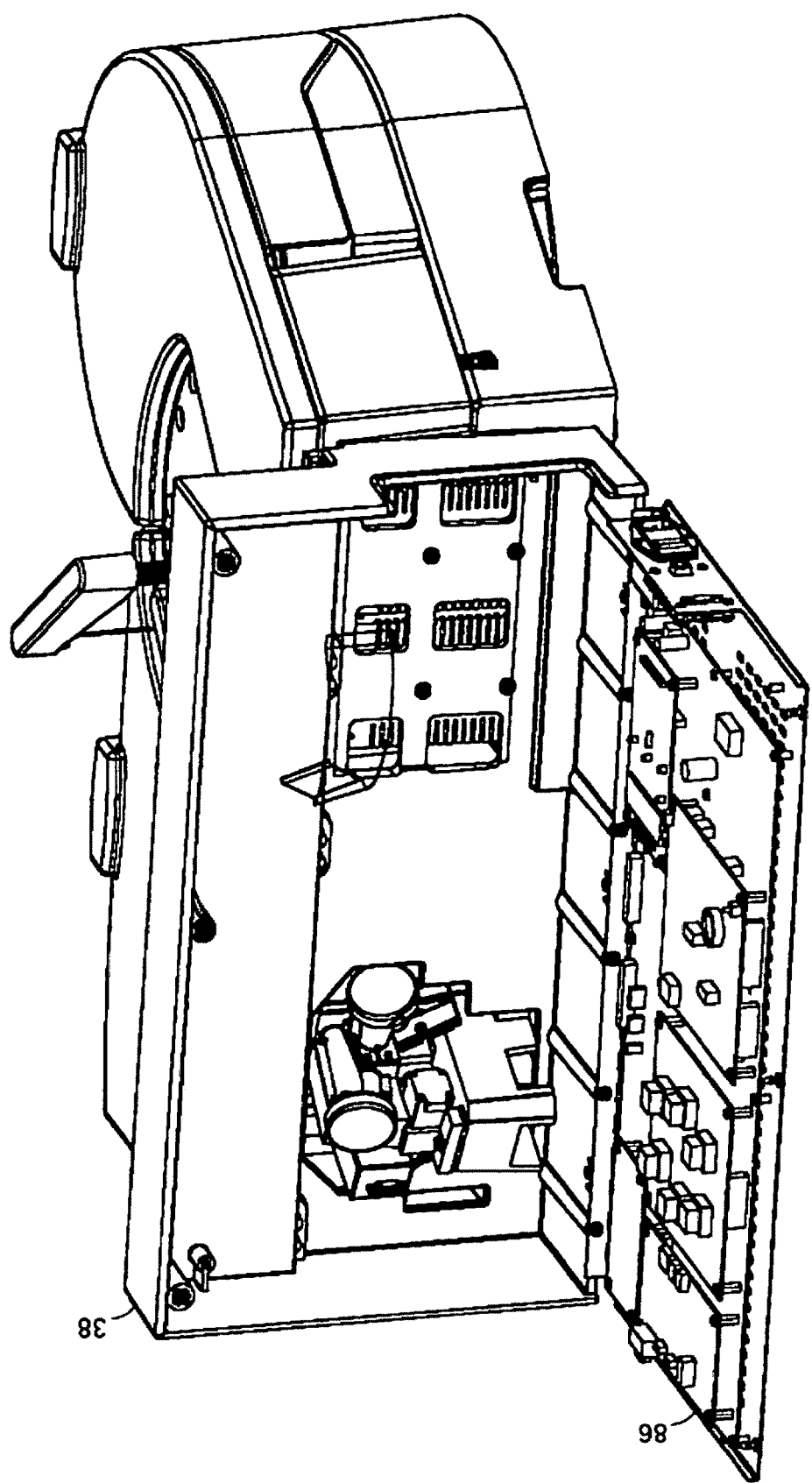
FIG. 9 is a rear perspective view of the chemistry analyzer of FIG. 1 with its electronics subassembly shown in its open position.

Referring to FIG. 8, to maintain precise positional tolerances, the base is also preferably reinforced, such as with webbing 88 and a stiffening plate 89. The use of a stiffening plate is an alternative to thick webbing, and it therefore reduces the overall height of the analyzer. The reinforced base is also solidly bolted to a rear portion that defines the electronics subsystem case 38, as shown in FIG. 9, to make it even stiffer.

Referring to FIG. 10, assembly of the analyzer includes the installation of the fan 57 for the optional cooling unit 58 in the sample/reagent area 12. This fan is held down with screws, but does not require pins or bosses.

Figure 11:
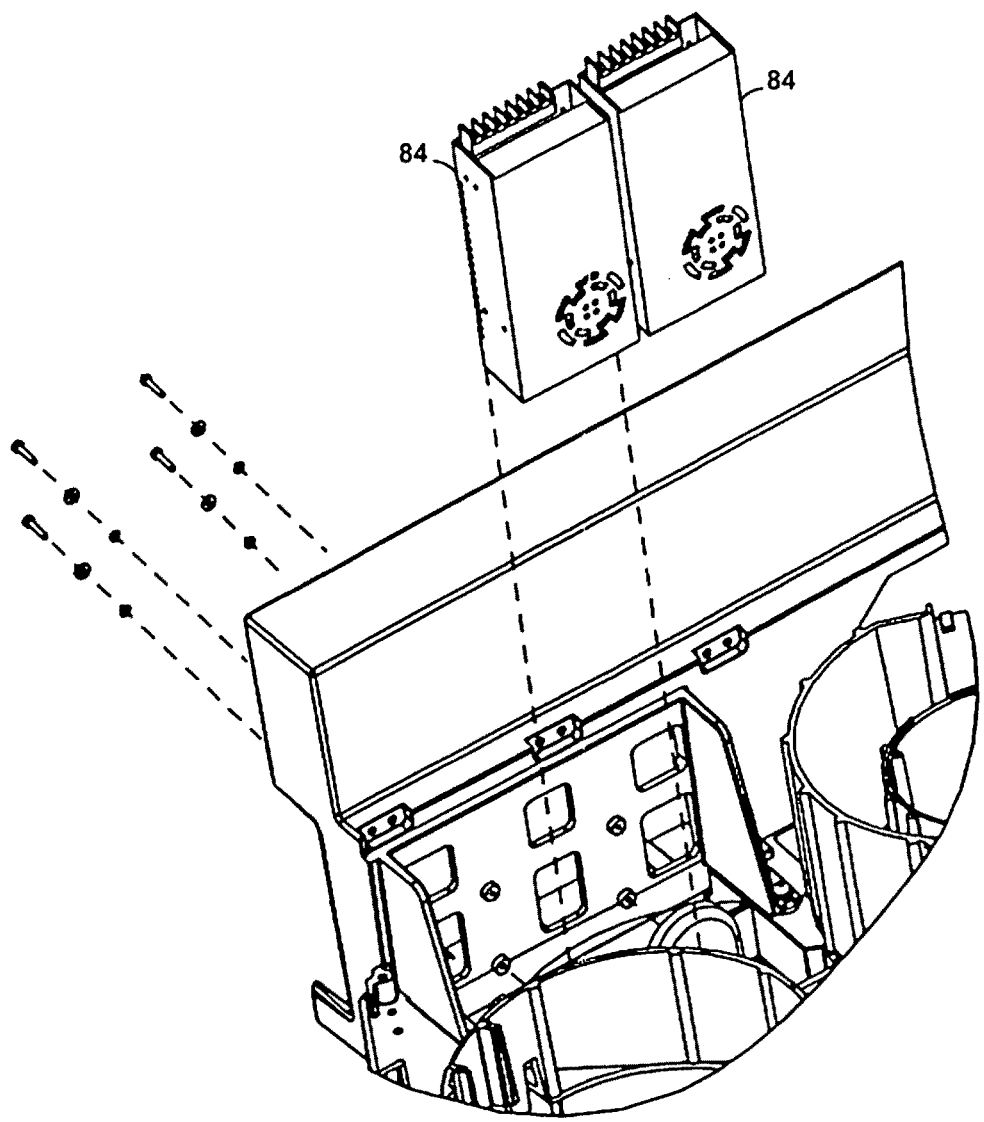
FIG. 11 is a partial perspective view of the illustrative modular chemistry analyzer of FIG. 1, showing the installation of its power supplies behind the reagent/sample area.

Referring to FIG. 11, the power supplies are inserted into an area behind the sample/reagent area. This location makes them relatively easy to replace. As discussed above, the power supplies do not require precise positioning, so no pins or bosses are provided for them. The power supply is connected to the various components that it supplies via a series of cables, which are preferably equipped with connectors, such as plug and socket connectors, to simplify assembly, disassembly, and servicing.

Figure 12:
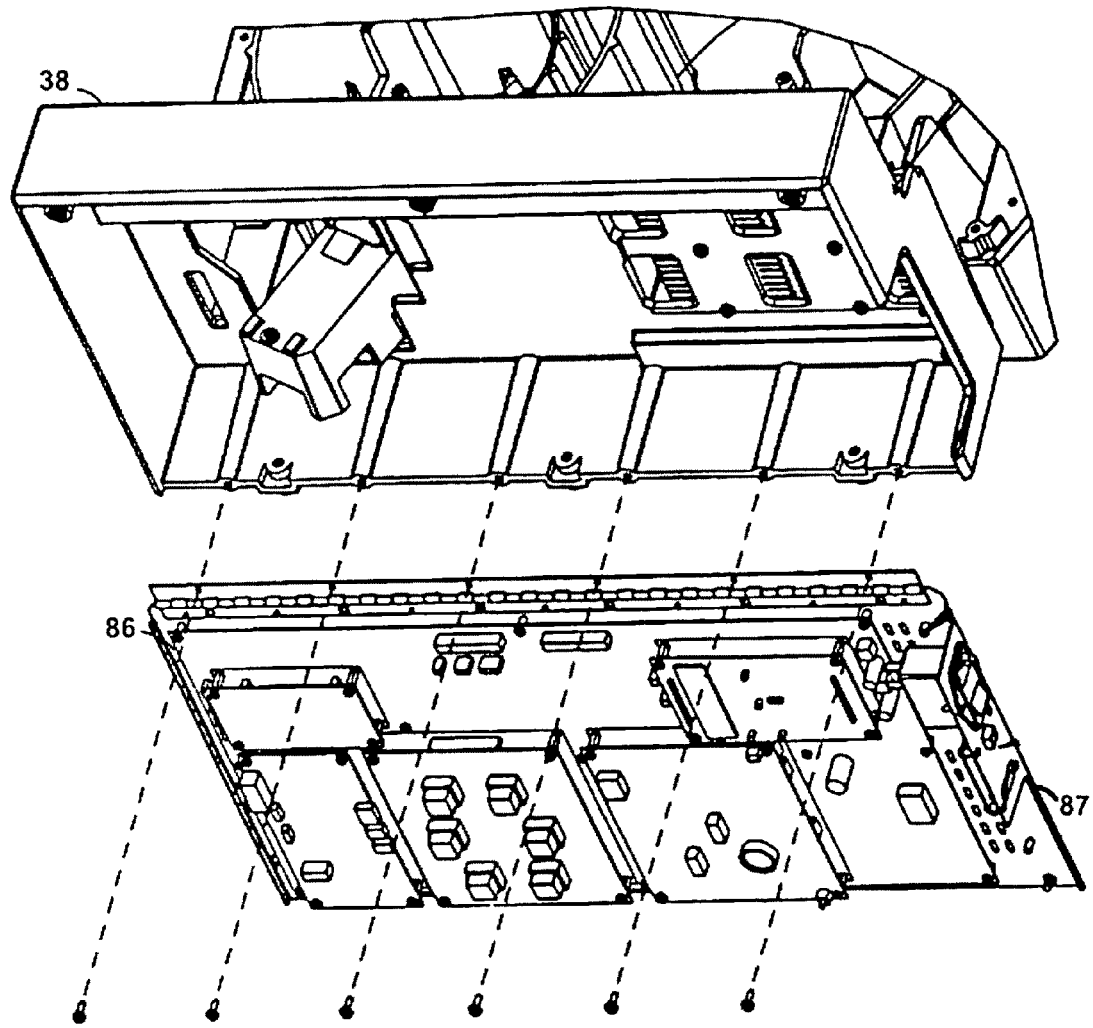
FIG. 12 is a rear-facing partial perspective view of the illustrative modular chemistry analyzer of FIG. 1, showing the installation of its electronics subassembly.

Referring to FIG. 12, the electronics subassembly 86 is made up of a mother board and daughter cards. The mother board is screwed to a hinged cover 87 for the case 38 at the back of the analyzer. In this highly accessible position, it is easy to diagnose failures, and/or repair or replace the assembly, its daughter cards, or other components.

The purpose of the electronic subassembly 86 is to control the operation of the analyzer and relay results to the operator. It is therefore electrically connected to various parts of the analyzer via a number of wires and/or cables. These are preferably equipped with connectors, such as plug-and-socket connectors, to simplify assembly, disassembly, and servicing.

Referring to FIG. 13, the reagent/sample tray drive and cooling subassembly 56 is screwed in place above the cooling unit fan 57 in the sample/reagent area 12 of the analyzer. As presented earlier, this subassembly is precisely positioned within the transfer arm's range using two pins and three bosses.

Figure 14:
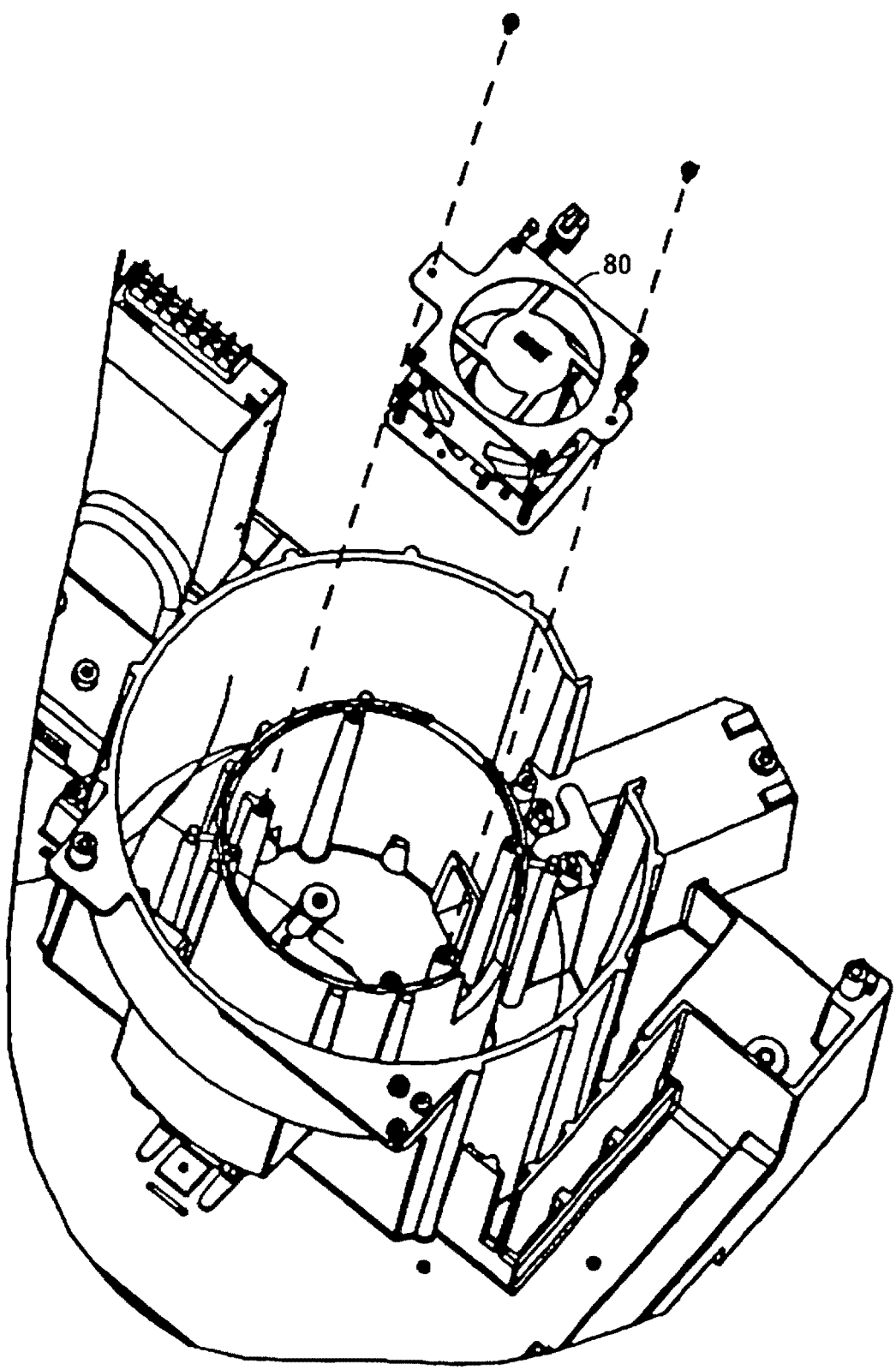
FIG. 14 is a partial perspective view of the illustrative modular chemistry analyzer of FIG. 1, showing the installation of its heater.

Referring to FIG. 14, the heater 80 is held in place in the reaction area by screwing it to two posts that are integral to the base 90. These height of these posts need not be precisely defined as the heater does not need to be positioned with a high degree of precision.

Figure 15:
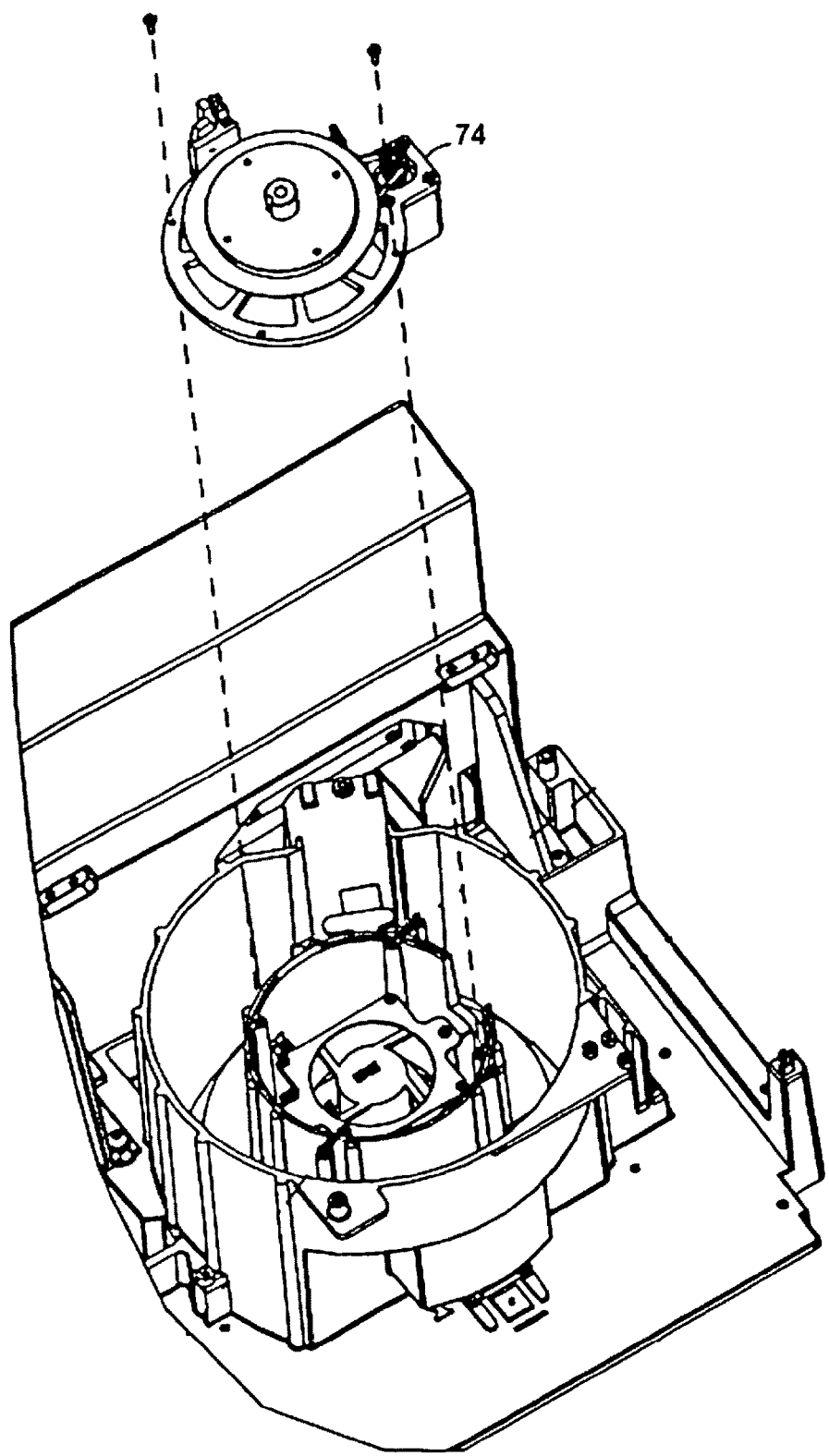
FIG. 15 is a partial perspective view of the illustrative modular chemistry analyzer of FIG. 1, showing the installation of its reaction area carousel drive subassembly.
Figure 16:
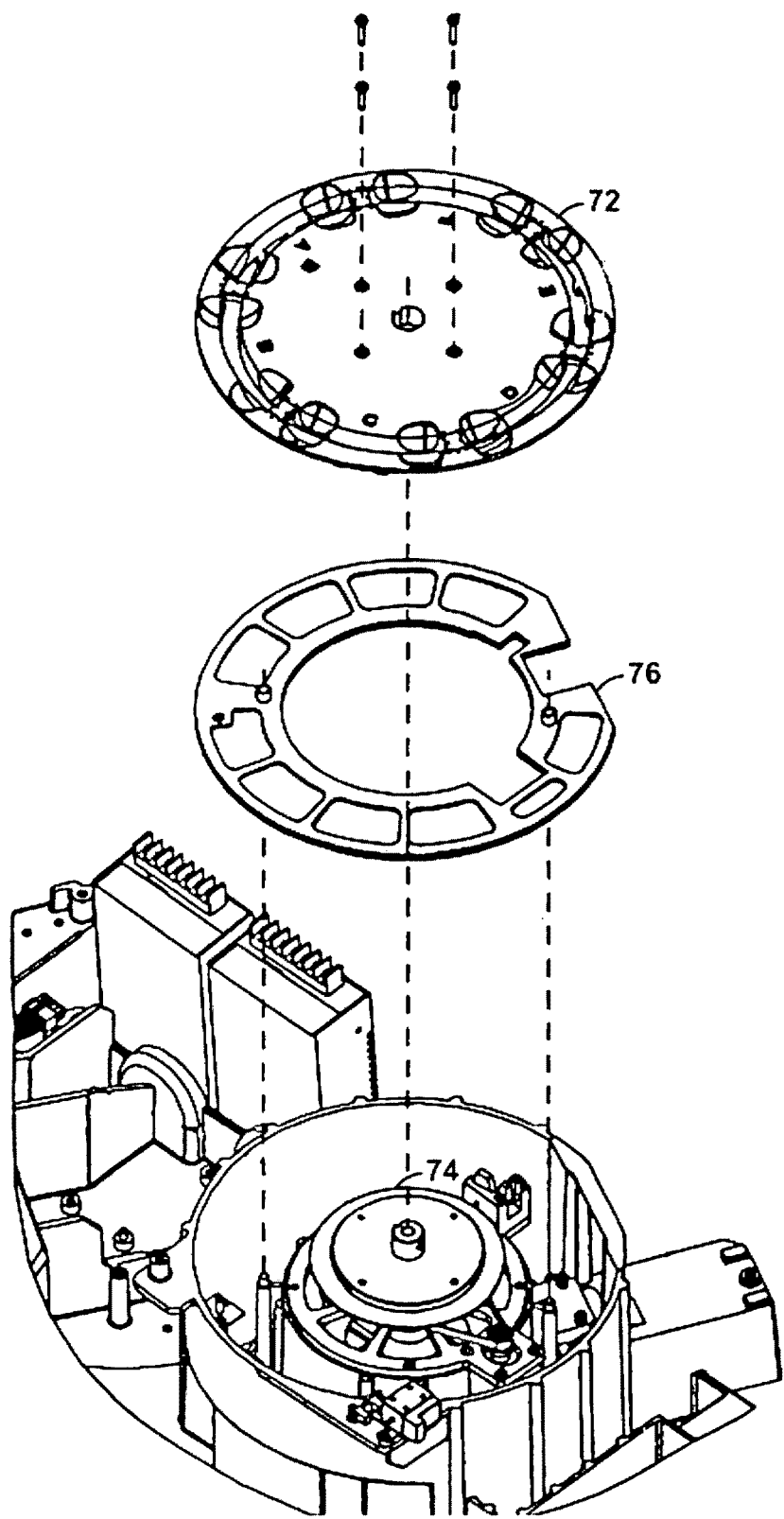
FIG. 16 is a partial perspective view of the illustrative modular chemistry analyzer of FIG. 1, showing the installation of its cuvette carousel and air filter above the reaction area carousel drive subassembly.

Referring to FIG. 15, the reaction area carousel drive subassembly 74 is screwed in place on three posts. These posts are precisely defined, such that some or all of their top surfaces can act as bosses, and two of them include pins. An air filter 78 is installed above the drive mechanism, and the cuvette wheel 72 can then be screwed to the reaction area carousel drive mechanism above the air filter, as shown in FIG. 16. The wheel holds disposable transparent reaction cuvettes ganged in groups of six.

Figure 17:
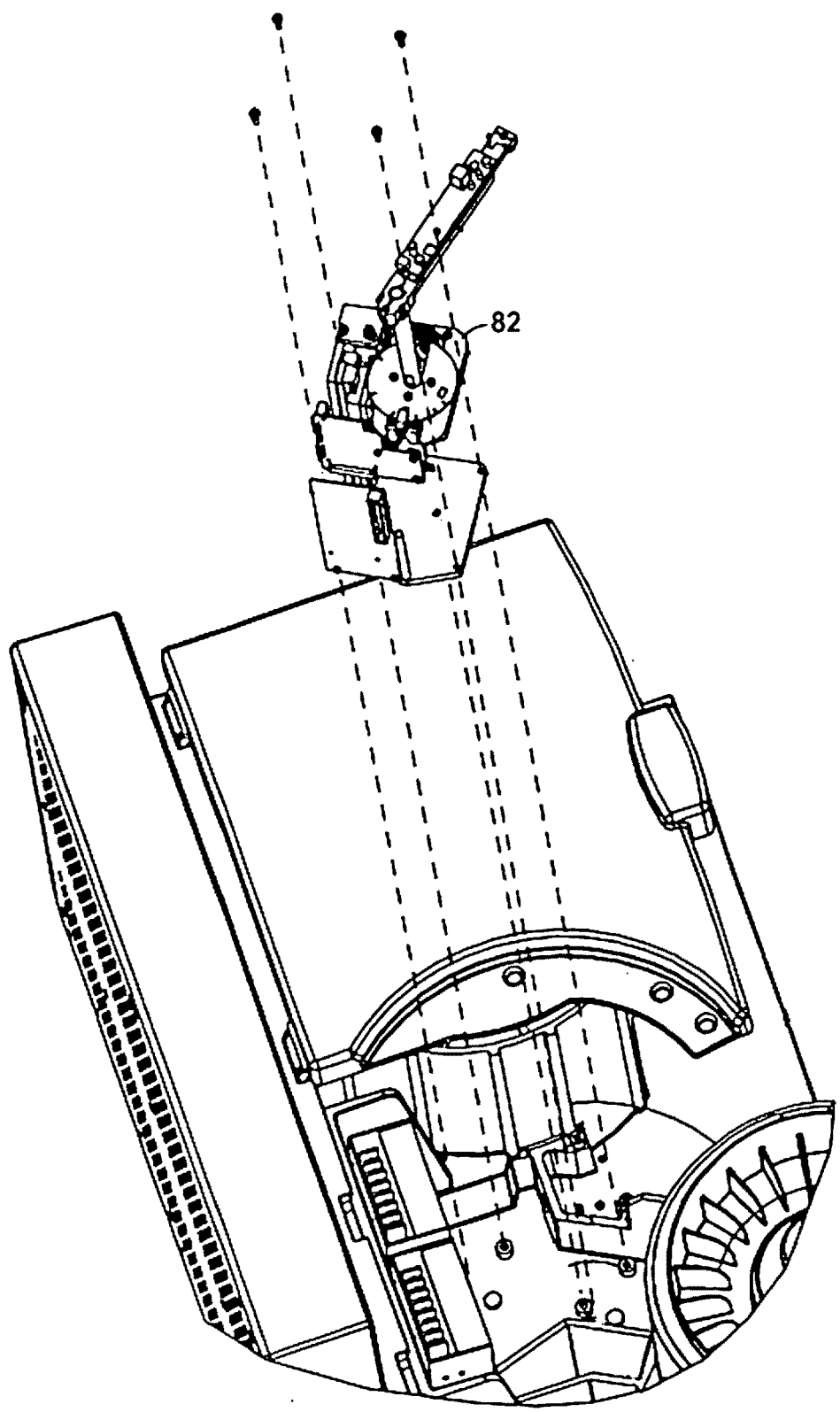
FIG. 17 is a partial perspective view of the illustrative modular chemistry analyzer of FIG. 1, showing the installation of its transfer arm subsystem.

Referring to FIG. 17, the transfer arm subassembly 82 is screwed onto a series of three bosses and constrained by two pins, with one of the pins being placed directly below the axis of rotation of the transfer arm. This precise positioning keeps the transfer arm and post at an exact relative position with respect to the various points that it needs to service, including one or more openings in the reagent and sample containers on the reagent/sample carousel, cuvettes on the cuvette carousel, the wash cup, and a sample cup on the ISE sensor module.

Figure 18:
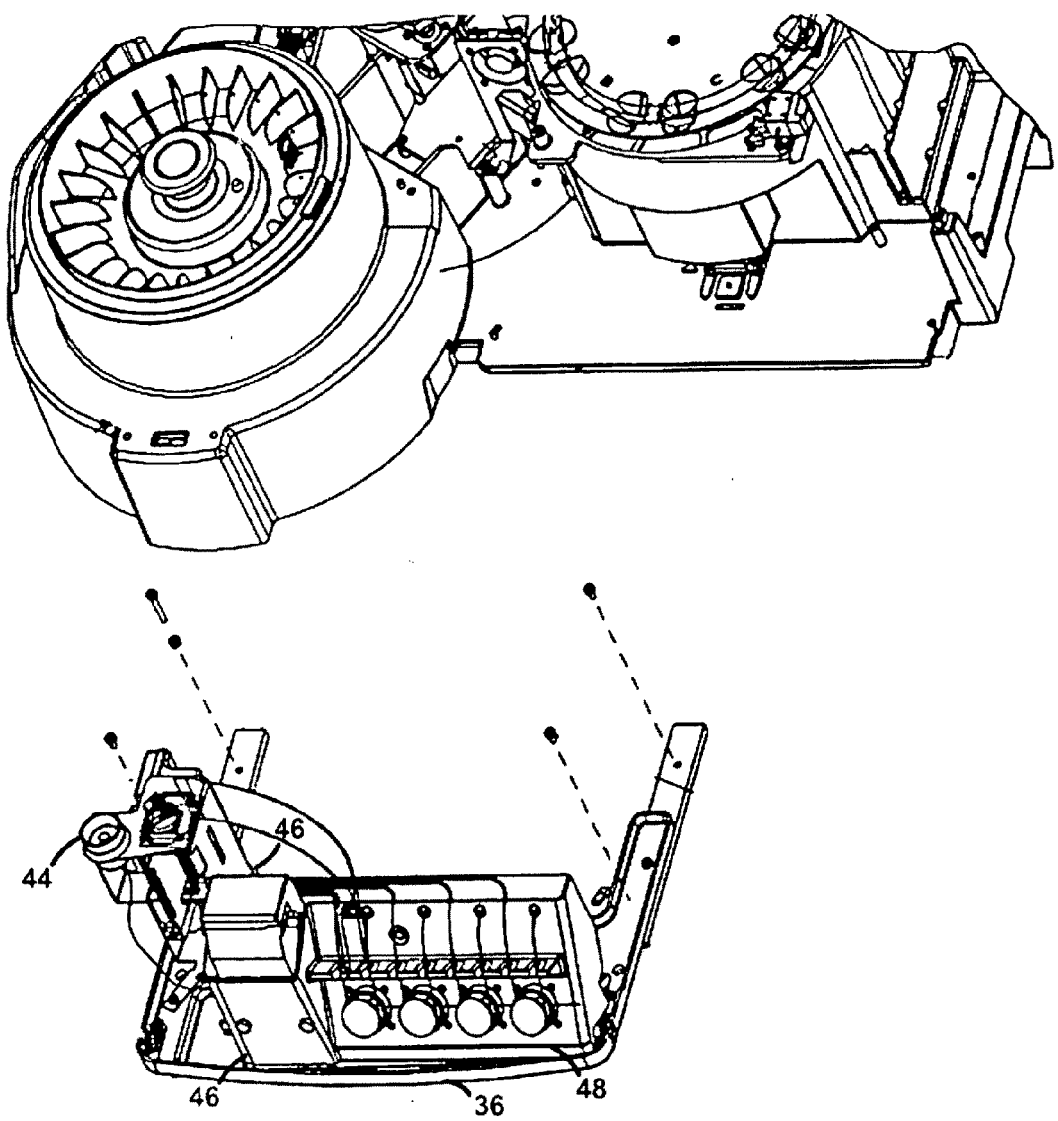
FIG. 18 is a partial perspective view of the illustrative modular chemistry analyzer of FIG. 1, showing the installation of its fluidics subsystem drawer base.

Referring to FIG. 18, the fluidics drawer base 36 is attached to the top of the base 90 of the unit with four screws. It is also constrained by bosses and pins to keep its ISE sensor module 42 and probe wash cup 44 precisely positioned within the transfer arm's range. One of the mounting screws is grounded.

Figure 19:
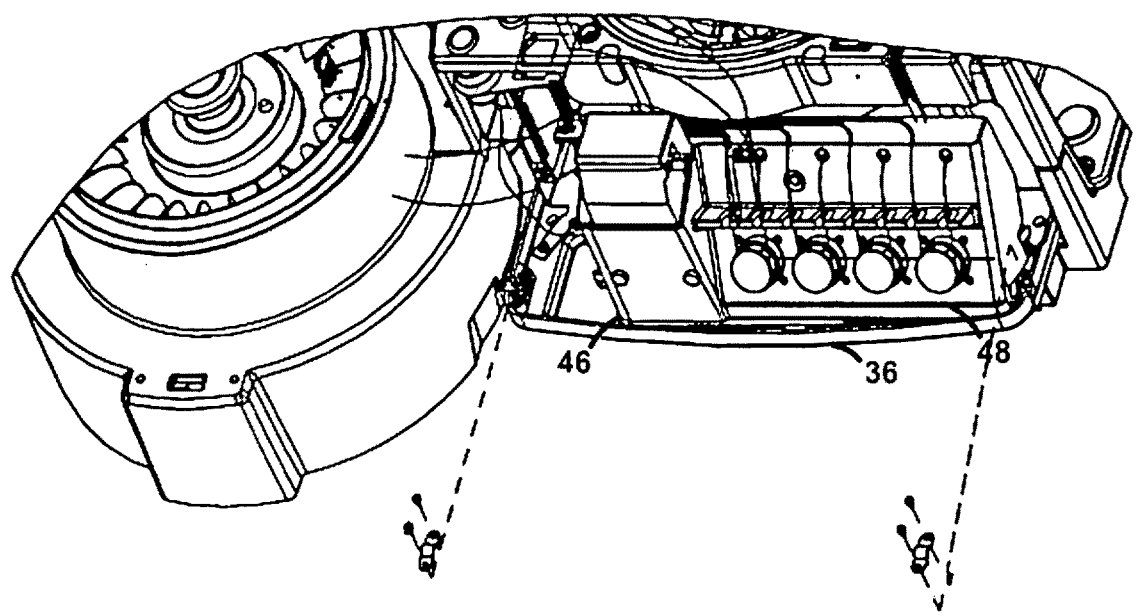
FIG. 19 is a partial perspective view of the illustrative modular chemistry analyzer of FIG. 1, showing the installation of its fluidics subsystem drawer front.
Figure 19:
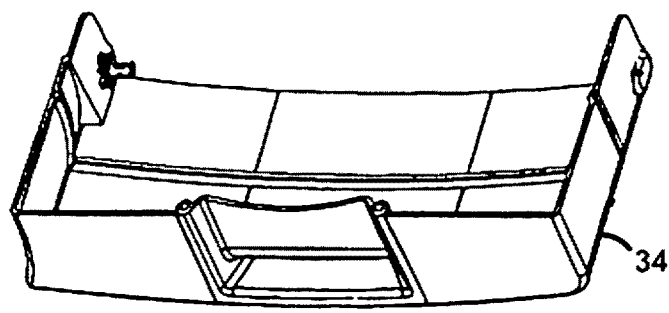

Referring to FIG. 19, the transparent pivoting fluidics drawer front 34 is pivotably mounted on the drawer base 36 using a pair of brackets and four screws. This component does not need to be constrained with a high degree of precision, since its only purpose is to act as a cover.

The use of a sliding fluidics drawer makes the fluidics subassembly easy to access and troubleshoot. Bubbles and blocked lines are clearly visible through the transparent cover 34 or with the drawer open, and some fluidics items may even be repaired or replaced without removing the analyzer's covers.

Figure 20:
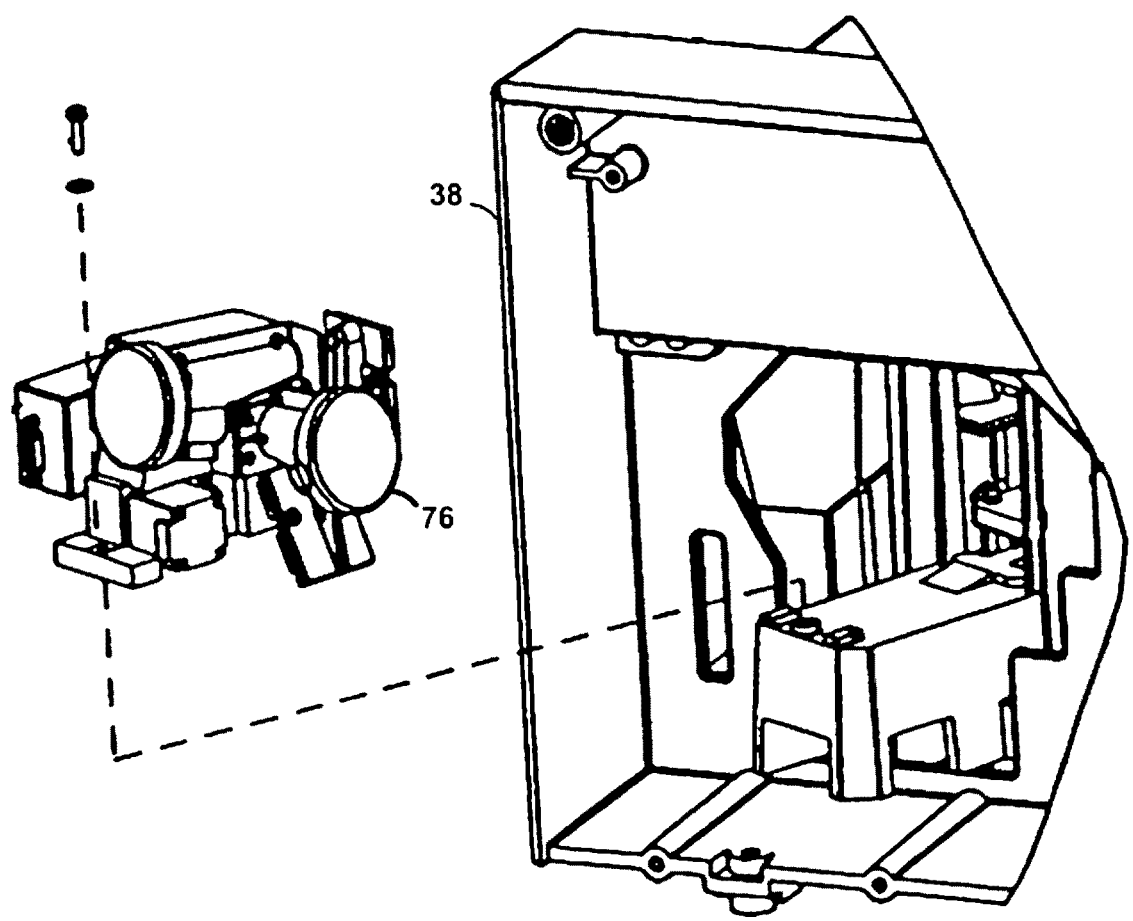
FIG. 20 is a partial perspective view of the illustrative modular chemistry analyzer of FIG. 1, showing the installation of its photometer.

Referring to FIG. 20, the photometer 76 is mounted on a pedestal 94 that is integral to the base at the rear of the reaction area. It is supported by two rear bosses and one front boss. A screw interfaces with a tapped insert between the two rear bosses to hold the photometer to its pedestal. This arrangement is sufficient to position the photometer with respect to the cuvette carousel and thereby allow it to take photometric measurements through the transparent cuvettes.

The assembly tasks described above cover the bulk of the assembly of the illustrative chemistry analyzer 10. One of ordinary skill in the art would of course recognize that there are a variety of smaller assembly steps, such as the attachment of covers and the installation of cables, hoses, and other small parts. But these details do not bear on the invention and have been omitted in the interest of clarity.

In operation, referring to FIGS. 1-3, the user begins by loading one or more reagent containers 62 in the reagent tray 52 and one or more disposable cuvettes in the cuvette wheel 72. The user also installs the sample ring 54 and any sample containers 60 that contain samples for analysis. After closing the reagent carousel cover, the analyzer performs a reagent inventory and/or a sample inventory (see FIG. 23 and accompanying text). The analyzer is now ready to carry out analysis tasks for the different samples using one or more reagents from one or more containers in the reagent tray.

Figures 21, 22:
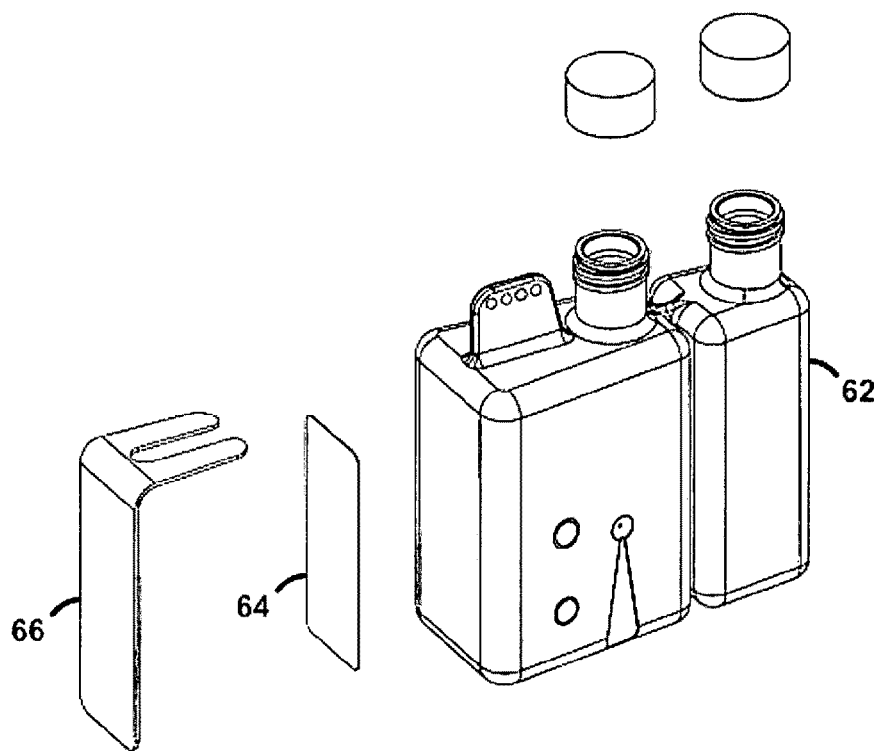
FIG. 21 is a perspective view of an illustrative two-part reagent container for use with the chemistry analyzer of FIG. 1.
FIG. 22 is an illustrative memory map for the illustrative reagent container for use with the chemistry analyzer of FIG. 1.

Referring to FIGS. 21-22, all of the information required to carry out the analysis sequence for each the reagents is contained in an RFID tag 64 under the label 66 of its reagent container 62. As shown in FIG. 22, this information can include: name, lot number, and expiration date, reagent volumes(s), reagent and sample blanking, analysis volumes for reagents, samples, and diluent, linear range of assay, primary and secondary wavelengths for photometric measurements, acceptable absorbance ranges, reaction read times, and urine parameters.

Storing all of this protocol information in the RFID tags in the reagent containers themselves can help to ensure that no test is ever conducted with an incorrect protocol. And there is no need to update the analyzer's software periodically to ensure that it is compatible with new tests. Instead, all of the information needed to run new tests and improvements to old tests can be simply read from the RFID tags on the reagent containers in the reagent tray, and the analyzer will use them correctly.

Storing the analysis protocol in the RFID tags on the reagent containers also has the advantage of allowing the container manufacturer to tailor the protocol for different reagent batches. If the manufacturer receives a reagent with a very slightly lower concentration than it specified, for example, reaction times can be slightly altered to correct for this discrepancy without any impact on precision or accuracy. This level of flexibility can even reduce the cost of producing reagents by relaxing the required tolerances for reagents. And it can increase the sensitivity of tests even if the reagents are within conventional, narrow ranges, by setting reaction parameters exactly for each batch instead of at a target nominal value that is good for all batches.

The RFID tags in the reagent containers can also store information received from the analyzer during operation, such as updated reagent volumes. Storing this information in the reagent containers can allow them to be moved from one analyzer to another or even allow them to survive computer failures without loss of reagent volume information. This can help to avoid a potentially serious situation in which no reagent of a particular type is on hand because the amount of reagent in existing containers was not known correctly.

Figure 23:
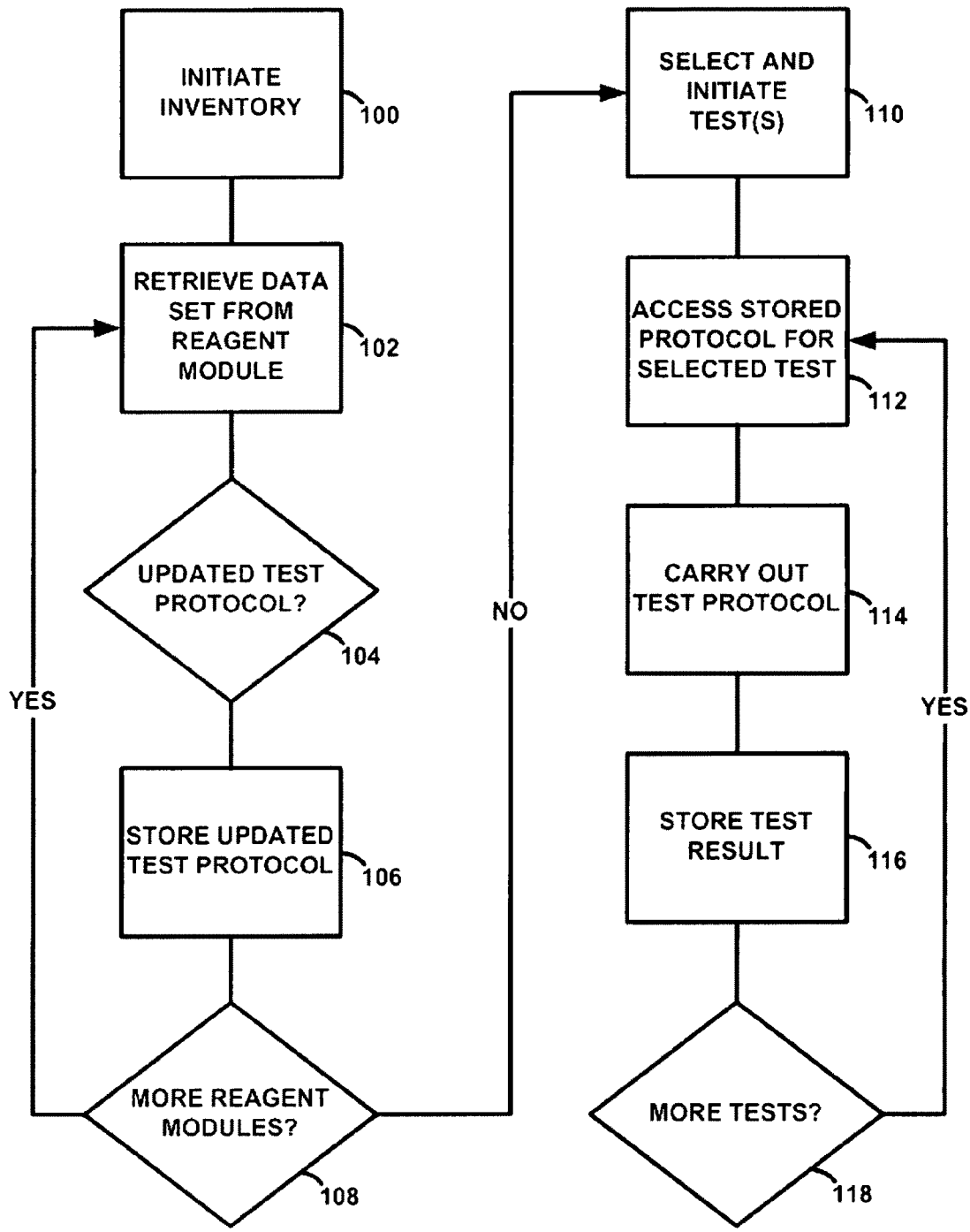
FIG. 23 is a flowchart illustrating the operation of the chemistry analyzer of FIG. 1.

Referring to FIG. 23, upon startup or user request, the analyzer initiates a reagent inventory operation in which the reagent tray is rotated to expose each of the reagent containers to the RFID reader 68 (step 100). The analyzer first retrieves the contents of a first tag (step 102). It can then check it to determine whether it holds a new protocol (step 104), and store it if it does (step 106). The test protocols can be stored in storage located in the analyzer housing, in storage located in the computer, or in another location, such as a central networked server. The inventory process is repeated for all of the reagent containers in the system (see step 108).

Once the protocols are stored, the system is ready to select and initiate analysis tasks (step 110). Each test begins with the analyzer accessing the stored test protocol corresponding to the reagent container to be used (step 112). The various subsystems then carry out the sequence of events in the test protocol (step 114). A sample and reagent might be mixed in a cuvette, for example, and the result tested using the photometer after a specified reaction read time. The test result is then stored (step 116), and further tests can be conducted for further samples (step 118).

The flowchart shown in FIG. 23 is illustrative only, and the inventory and test operations can take place according to other sequences. It may make sense in some instances to simply record all protocol data for all reagent containers, for example, even if data for some or all of them is redundant. Analysis tasks may also be interleaved to save time.

Inventory initiation can be made mandatory each time that reagents and/or samples could be removed from the system. For example, the inventory can be initiated each time the cover 30 for the reagent/sample carousel subassembly is closed. This interlock mechanism can prevent errors by ensuring that regent or sample containers are not replaced, moved, or removed before testing begins.

Figure 24:
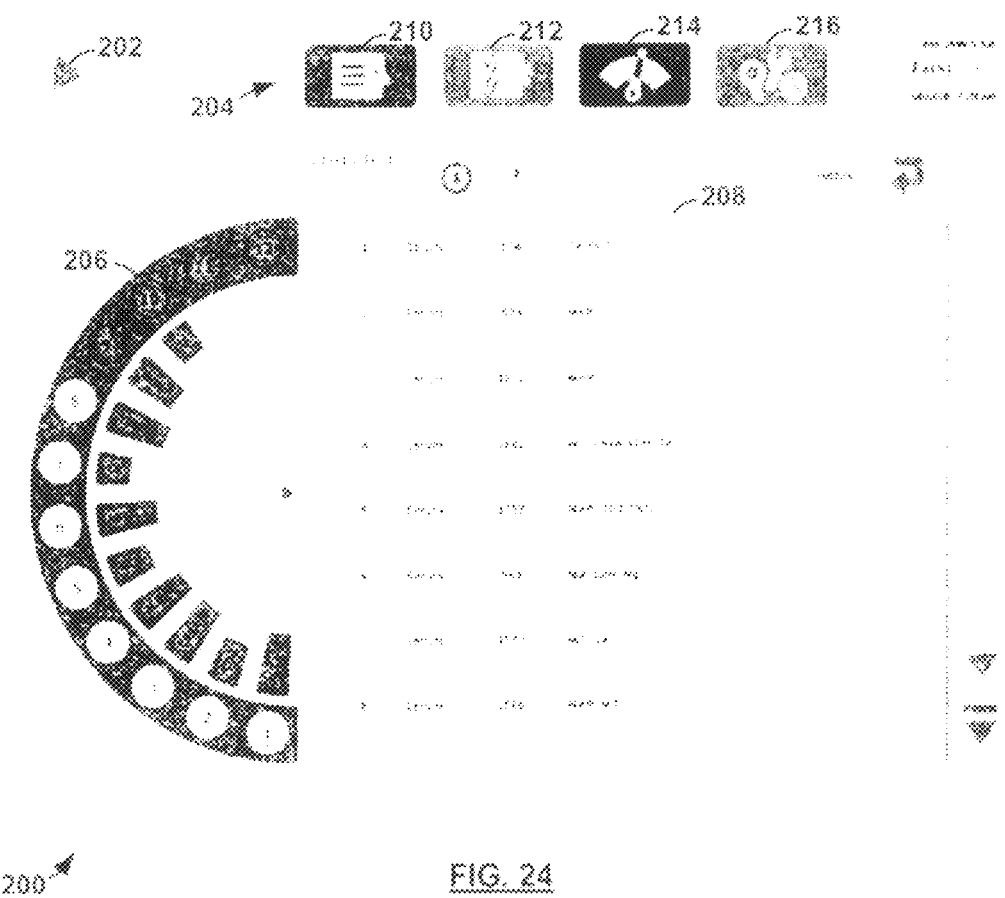
FIG. 24 is a screenshot of a worklist screen for the chemistry analyzer of FIG. 1.

Referring to FIG. 24, the operator can interact with the analyzer 10 through a series of software-generated views presented on the touch screen 22. The worklist screen 200, for example, includes one or more status icons 202, an icon bar 204, a visual representation 206 of half of the reagent tray 52/sample ring 54, and a data table 208. The visual representation shows what reagent containers are in the reagent tray based on the results of an earlier inventory, by displaying a series of wedge shapes that are similar to the shape of the reagent containers. It also shows occupied positions in the sample ring as white numbered circles and unoccupied positions in shaded circles positioned in a semicircular area that is similar to the sample ring. The quantity of reagent left in each reagent container is shown as a shaded area that resembles a fill level in the wedge shape, and the reagent containers are identified by standard abbreviations (e.g., Ca for calcium). The data table shows a list of tests that correspond to the different sample areas, which are referenced by their numbers in the visual representation. Together, the elements of the worklist screen allow the user to quickly understand the status of the system and the run of tests that is about to begin.

The icon bar 204 includes four differently colored icons that divide the operation of the system into four functional areas. Touching these icons leads the user to menus allowing him or her to select from a series of sub-screens in each of these areas. Each of the sub-screens is color coded to remind the user what type of task he or she is performing.

This approach of using a combination of color coding and visual representations helps orient the user and avoid errors. This can be particularly helpful for users for whom the language used by the analyzer is a second language. It also allows the analyzer to use text more sparsely, which is beneficial for models deployed in a variety of different markets, as the user interface can be designed with little or no text that needs to be translated.

In one embodiment, the four icons include a worklist icon 210 (blue), a results icon 212 (orange), a status icon 214 (green), and a diagnostics/maintenance/setup icon 216 (pink). The worklist group accessible from the worklist icon 210 includes a view LIS list entry, an edit worklist entry, a monitor worklist entry, a view pending list entry, and an ISE calibration entry. The results group accessible from the results icon 212 includes a current results entry, a last results entry, a patient results entry, calibration results entry, a quality control results entry, and an other tables entry. The status group accessible from the status icon 214 includes a worklist warnings entry, a reagents entry, a calibration entry, a quality control entry, a cuvettes entry, an ISE entry, a cleaning entry, an inventory report entry, and a sample inventory entry. The diagnostics/maintenance/setup group accessible from the diagnostics/maintenance/setup icon 216 includes a cleaning entry, a diagnostics entry, a maintenance entry, and a setup entry. The setup entry includes sub-entries for system, tests, patient, calibration, quality control, and reagent. One of ordinary skill in the art will recognize that the exact breakdown of the screens is highly dependent on the detailed characteristics of the particular chemistry analyzer, and that there are a variety of different, reasonable ways to organize the screens for a given analyzer.

The various tasks performed by the analyzer can be carried using a specially programmed general purpose computer, dedicated hardware, or a combination of both. In one embodiment, the system is based on a Microsoft Windows®-based computer system, but other platforms could be used as well, such as Apple McIntosh®, Linux®, or UNIX®-based platforms. And while the touch screen is a currently a preferred user interface device, other types of devices could also be used, such as mice, keyboards, or trackballs. Other embodiments can even employ a simple, hardwired keypad instead of a computer.

The present invention has now been described in connection with a number of specific embodiments thereof. However, numerous modifications which are contemplated as falling within the scope of the present invention should now be apparent to those skilled in the art. It is therefore intended that the scope of the present invention be limited only by the scope of the claims appended hereto. In addition, the order of presentation of the claims should not be construed to limit the scope of any particular term in the claims.

What is claimed is:

1. A chemistry analyzer, including:
    I. a molded unitary base, for mounting a plurality of subassemblies that include at least:
        a reagent/sample carousel subassembly for holding reagents for testing different selected analytes in blood and for holding samples of different patients,
        a reaction carousel subassembly that defines cuvette locations,
        a transfer arm subassembly including a probe for transferring reagents and samples to the cuvette locations,
        a wash station positioned along an arc of motion of the transfer arm, and
        a photometer positioned to acquire photometric measurements from the cuvette locations in the reaction carousel,
    II. wherein the base includes:
        A. a plurality of vertical supports that are integral to the unitary base and include:
            at least one vertical support for the reagent/sample carousel subassembly to constrain a vertical axis of the reagent/sample carousel subassembly at a predetermined position in a horizontal plane,
            at least one vertical support for the transfer arm subassembly to constrain a vertical axis of the transfer arm subassembly at a predetermined position in the horizontal plane relative to the vertical axis of the reagent/sample carousel,
            at least one vertical support for the reaction carousel subassembly to constrain a vertical axis of the reaction carousel subassembly at a predetermined position in the horizontal plane relative to the vertical axis of the transfer arm, at least one vertical support for the wash station to constrain a vertical axis of the wash station at a predetermined position in the horizontal plane relative to the vertical axis of the transfer arm, and at least one vertical support for the photometer to constrain the photometer at a predetermined position in the horizontal plane relative to a vertical axis of the cuvette locations defined by the reaction carousel, and B. a plurality of horizontal supports that are integral to the unitary base and include:

at least three horizontal supports for the reagent/sample carousel subassembly to constrain the reagent/sample carousel subassembly at a predetermined position in the vertical direction, at least three horizontal supports for the transfer arm subassembly to constrain the transfer arm subassembly at a predetermined position in the vertical direction relative to the horizontal position of the reagent/sample carousel, at least three horizontal supports for the reaction carousel subassembly to constrain the reaction carousel subassembly at a predetermined position in the vertical direction relative to the horizontal position of the reagent/sample carousel, at least three horizontal supports for the wash station to constrain the wash station at a predetermined position in the vertical direction relative to the vertical position of the transfer arm, at least three horizontal supports for the photometer to constrain the beam of the photometer subassembly at a predetermined position in the vertical direction relative to a vertical position of the cuvette locations defined by the reaction carousel, and wherein the horizontal supports for at least a first of the subassemblies are at different vertical positions from the horizontal supports for at least a second of the subassemblies, and III. whereby the base holds the reagent/sample carousel subassembly, the transfer arm subassembly, the wash station, and the photometer fixed relative to the cuvette locations defined by the reaction carousel subassembly in a single integrated unit.

2. The apparatus of claim 1 wherein the horizontal supports are each defined by a single boss.

3. The apparatus of claim 1 wherein a plurality of the horizontal supports for at least one of the subassemblies are provided by a single support surface.

4. The apparatus of claim 1 wherein the vertical supports are each defined by a single pin.

5. The apparatus of claim 1 wherein the base includes two vertical supports for at least one of the subassemblies to constrain rotation of that subassembly.

6. The apparatus of claim 1 wherein the base portions include at least a paired boss and pin for each of the subassemblies, with the paired pin being positioned to protrude above the paired boss.

7. The apparatus of claim 1 wherein at least two pins define vertical supports for the reagent/sample carousel subassembly, at least two pins define vertical supports for the reaction area subassembly, and at least one pin defines the vertical support for the transfer arm subassembly.

8. The apparatus of claim 1 wherein the base comprises a single molded base part with the horizontal supports being machined on horizontal areas of the single molded base part.

9. The apparatus of claim 1 wherein the horizontal and vertical supports fully constrain each of the subassemblies independent of any fastening mechanism.

10. The apparatus of claim 1 wherein the subassemblies include a reagent/sample carousel subassembly, a transfer arm subassembly, and a reaction carousel subassembly.

11. The apparatus of claim 1 wherein the base comprises a single molded thermoplastic base part.

12. The apparatus of claim 1 wherein the vertical supports are each defined by a single pin inserted in a hole in the base.

13. The apparatus of claim 1 wherein the horizontal supports for the photometer are at different vertical positions from the horizontal supports for the reaction carousel subassembly.

14. The apparatus of claim 13 wherein the horizontal supports for the transfer arm subassembly are at different vertical positions from the horizontal supports for the carousel subassemblies.

15. The apparatus of claim 14 wherein the horizontal supports for the transfer arm subassembly are at different vertical positions from the horizontal supports for the photometer.

16. The apparatus of claim 13 wherein the horizontal supports for reagent/sample carousel subassembly are at different vertical positions from the horizontal supports the reaction carousel subassembly.

17. The apparatus of claim 1 wherein the horizontal supports for the transfer arm subassembly are at different vertical positions from the horizontal supports for the carousel subassemblies.

18. The apparatus of claim 1 wherein the horizontal supports for all of the subassemblies are at different vertical positions from the horizontal supports for all of the other subassemblies.

* * * * *